(12) United States Patent
Rothman et al.

(10) Patent No.: US 8,100,829 B2
(45) Date of Patent: *Jan. 24, 2012

(54) SYSTEM AND METHOD FOR PROVIDING A HEALTH SCORE FOR A PATIENT

(75) Inventors: Michael J. Rothman, Hopewell Juntion, NY (US); Steven I. Rothman, Monticello, NY (US); Daniel B. Rothman, Santa Barbara, CA (US)

(73) Assignee: Rothman Healthcare Corporation, Sarasota, FL (US)

( * ) Notice: Subject to any disclaimer, the term of this patent is extended or adjusted under 35 U.S.C. 154(b) by 152 days.

This patent is subject to a terminal disclaimer.

(21) Appl. No.: 11/974,696

(22) Filed: Oct. 15, 2007

(65) Prior Publication Data

US 2009/0105550 A1    Apr. 23, 2009

Related U.S. Application Data

(60) Provisional application No. 60/851,835, filed on Oct. 13, 2006.

(51) Int. Cl.
*A61B 5/00* (2006.01)
*G06Q 10/00* (2012.01)
*G06Q 50/00* (2012.01)

(52) U.S. Cl. ............ 600/300; 600/301; 705/2; 705/3

(58) Field of Classification Search .............. None
See application file for complete search history.

(56) References Cited

U.S. PATENT DOCUMENTS 5,074,980 A    12/1991  Vasta-Russell et al. ...... 204/182
5,850,339 A    12/1998  Giles
6,193,654 B1 *  2/2001  Richardson et al. .......... 600/300
6,336,903 B1    1/2002  Bardy (Continued)

FOREIGN PATENT DOCUMENTS

GB      2 392 750       10/2004

(Continued)

OTHER PUBLICATIONS

Reintam et al. "Gastrointestinal failure in intensive care: a retrospective clinical study in three different intensive care units in Germany and Estonia" BMC Gastroenterology © 2006.*

(Continued)

*Primary Examiner* — Sam Yao
*Assistant Examiner* — Shirley Jian
(74) *Attorney, Agent, or Firm* — Greenberg Traurig, LLP; David J. Dykeman; Danielle T. Abramson

(57) ABSTRACT

A system and method for providing an indicator of a patient's health. The system may include a data module receiving data relating to a patient's health, the data including subjective data, a conversion module generating an output from the data, the output representing the patient's health, and a display module displaying the output and a standard output for a user to compare with the output. A method of providing a customizable system for generating an indicator of a patient's health, the method including providing a system including a data module, a conversion module generating an output via a first algorithm, and a display module displaying the output and a standard output generated by a second algorithm, and customizing at least one of the first and second algorithms according to preferences of a user.

20 Claims, 14 Drawing Sheets

U.S. PATENT DOCUMENTS

| | | | |
|---|---|---|---|
| 6,438,419 B1 | 8/2002 | Callaway et al. | 607/5 |
| 6,790,178 B1 | 9/2004 | Mault et al. | 600/300 |
| 6,960,167 B2 | 11/2005 | Bardy | |
| 7,003,341 B2 | 2/2006 | Say et al. | 600/345 |
| 7,031,857 B2 | 4/2006 | Tarassenko et al. | 702/67 |
| 7,081,091 B2 | 7/2006 | Merrett et al. | |
| 7,213,009 B2 | 5/2007 | Pestotnik et al. | 706/46 |
| 7,454,359 B2 | 11/2008 | Rosenfeld et al. | |
| 2002/0026104 A1 | 2/2002 | Brady | 600/300 |
| 2003/0208106 A1 | 11/2003 | Anderson et al. | |
| 2003/0225315 A1 | 12/2003 | Merrett et al. | |
| 2005/0187796 A1 | 8/2005 | Rosenfeld et al. | 705/3 |
| 2006/0161459 A9 | 7/2006 | Rosenfeld et al. | 705/3 |
| 2006/0200009 A1 | 9/2006 | Wekell et al. | |
| 2006/0206012 A1* | 9/2006 | Merrett et al. | 600/300 |
| 2006/0206013 A1 | 9/2006 | Rothman et al. | 600/300 |
| 2006/0287906 A1 | 12/2006 | McGillin | 705/9 |
| 2010/0100392 A1 | 4/2010 | Rothman et al. | |

FOREIGN PATENT DOCUMENTS

| | | |
|---|---|---|
| WO | WO 02/21313 | 3/2002 |
| WO | WO 03/082097 | 10/2003 |
| WO | WO 2006/093807 | 9/2006 |
| WO | WO 2008/045577 | 4/2008 |
| WO | WO 2010/048282 A1 | 4/2010 |

OTHER PUBLICATIONS

"Braden Scale for Predicting Pressure Sore Risk" © Barbara Braden and Nancy Bergstrom 1988.*

Cathy, Jones "Glasgow Coma Scale" The American Journal of Nursing, vol. 79, No. 9 (Sep. 1979), pp. 1551-1553.*

Abraham, Edward, "Glucose-6-Phosphate Dehydrogenase and Sepsis: The Jury is Still Out", Crit Care Med., Editorial, vol. 35, No. 2 (2007) pp. 655-656.

Aiken et al., "Hospital Nurse Staffing and Patient Mortality, Nurse Burnout, and Job Dissatisfaction", JAMA, vol. 288, No. 16 (Oct. 23/30, 2002) pp. 1987-1993.

Alam, Hasan B., "To Cool or Not to Cool, That is the Question", Crit Care Med., Editorial, vol. 35, No. 2 (2007) pp. 660-662.

Aneman et al., "The ERC Guidelines for Resuscitation 2005 and the Medical Emergency Team", Scand J Trauma Resusc Emerg Med, vol. 14 (2006), pp. 74-77.

Asai, Takashi, "How Should We Use Prokinetic Drugs in Patients who are Intolerant to Enteral Feeding?", Crit Care Med., Editorial, vol. 35, No. 2 (2007) pp. 650-651.

Baggs, Judith G., "Nurse-Physician Collaboration in Intensive Care Units", Crit Care Med., Editorial, vol. 35, No. 2 (2007) pp. 641-642.

Baggs, Judith G., "Prognostic Information Provided During Family Meetings in the Intensive Care Unit", Crit Care Med., Editorial, vol. 35, No. 2 (2007) pp. 646-647.

Bates et al., "Improving Safety with Information Technology", N Engl J Med, vol. 348, No. 25 (Jun. 19, 2003) pp. 2526-2534.

Bensen et al., "To be or Not to be (In the Intensive Care Unit)-Is that a Question?", Crit Care Med., Editorial, vol. 35, No. 2 (2007) pp. 647-648.

Berman et al., "Validation of the 2000 Bernstein-Parsonnet Score Versus the EuroSCORE as a Prognostic Tool in Cardiac Surgery", Ann Thorac Surg, vol. 86 (2006) pp. 537-541.

Berms, John J., "Ischemia-Reperfusion: Putting the Pieces of the Puzzle Together", Crit Care Med., Editorial, vol. 34, No. 5 (2006) pp. 1570-1571.

Bion et al., "Improving the Reliability of Healthcare Systems' Responsiveness to the Needs of Acutely Ill Patients", Crit Care Med., Editorial, vol. 35, No. 2 (2007) pp. 637-639.

Braden et al., "Braden Scale for Predicting Pressure Sore Risk" (1988).

Brander et al.. "Exophageal and Transpulmonary Pressure Help Optimize Mechanical Ventilation in Patients with Acute Lung Injury", Crit Care Med., Editorial, vol. 34, No. 5 (2006) pp. 1556-1558.

Brennan et al., "Accidental Deaths, Saved Lives, and Improved Quality", N Engl J Med, vol. 353, No. 13 (Sep. 29, 2005) pp. 1405-1409.

Clark et al., "Concurrent Prediction of Hospital Mortality and Length of Stay From Risk Factors on Admission", vol. 37, No. 3 (Jun. 2002) pp. 631-645.

Clinton et al., "Making Patient Safety the Centerpiece of Medical Liability Reform", N Engl J Med, vol. 354, No. 21 (May 25, 2006), pp. 2205-2208.

Cole, Randolph P., "Predicting Response to Fluid Administration: Something Old, Something New?", Crit Care Med., Editorial, vol. 34, No. 5 (2006) pp. 1559-1560.

Coimbra, Raul, "Salt in the Vein, Good for the Brain . . . ", Crit Care Med., Editorial, vol. 35, No. 2 (2007) pp. 659-660.

Cretikos et al., "The Objective Medical Emergency Team Activation Criteria: A Case-Control Study", Resuscitation, Vo.. 73 (2007) pp. 62-72.

Crippen, David, "Comfortably Numb in the Intensive Care Unit", Crit Care Med., Editorial, vol. 34, No. 5 (2006) pp. 1558-1559.

Cuthbertson, B.H., "Can Physiological Variables and Early Warning Scoring Systems Allow Early Recognition of the Deteriorating Surgical Patient?", Crit Care Med, vol. 35, No. 2 (2007) pp. 402-409.

Cuthbertson, B.H., "Editorial II: Outreach Critical Care-Cash for No Questions", British Journal of Anesthesia, Editorial II (2003) pp. 4-6.

DeVita et al., "Findings of the First Consensus Conference on Medical Emergency Teams", Crit Care Med, vol. 34, No. 9 (2006) pp. 2463-2478.

Dupuydt et al., "Antiobiotic Therapy for Ventilator-Associated Pneumonia: De-Escalation in the Real World", Crit Care Med., Editorial, vol. 35, No. 2 (2007) pp. 632-633.

Engle, Toby R. MD "Electrocardiographic Diagnosis of Coronary Syndromes in the Critical Care Unit", Crit Care Med., Editorial, vol. 34, No. 5 (2006) pp. 1546-1547.

Epstein, Scott K, MD "Preventing Prostextubation Respiratory Failure", Crit Care Med., Editorial, vol. 34, No. 5 (2006) pp. 1547-1548.

Erikkson, Urs, "Chlamydia and Myocarditis: An Old Bug Bugging Seriously", Crit Care Med., Editorial, vol. 35, No. 2 (2007) pp. 665.

Finster et al., "The Apgar Score has Survived the Test of Time", Anesthesiology, Vo. 102, No. 4 (Apr. 2005) pp. 855-857.

Forster et al., "Adverse Events Among Medical Patients After Discharge", CMAJ, vol. 170, No. 3 (Feb. 3, 2004) pp. 345-349.

Fraser et al., "Comfort without Coma: Changing Sedation Practices", Crit Care Med., Editorial, vol. 35, No. 2 (2007) pp. 635-637.

Friedman et al., "The Rate and Cost of Hospital Readmissions for Preventable Conditions", MCR&R, vol. 61, No. 2 (Jun. 2004), pp. 225-240.

Gao et al., "Systematic Review and Evaluation of Physiological Track and Trigger Warning Systems for Identifying At-Risk Patients on the Ward", Intensive Care Med, vol. 33 (2007) pp. 667-679.

Gentilello, Larry M., "Alcohol and the Intensive Care Unit: It's Not Just an Antiseptic", Crit Care Med., Editorial, vol. 35, No. 2 (2007) pp. 627-628.

Gogbashian et al., "EuroSCORE: A Systematic Review of International Performance", European Journal of Cario-thoracic Surgery, vol. 25 (2004) pp. 695-700.

Goldhill, David R., "Editorial: Of Missiles and Medicine: Early Warning Systems", Anesthesia, vol. 61 (2006) pp. 209-214.

Goldhill et al., "Physiological Values and Procedures in the 24 h Before ICU Admission from the Ward", Anesthesia, vol. 54 (1999) pp. 529-534.

Goldstein, Brahm, "How Do We Get From Here to There? A Pathway for Trial Design in Complex Systems Analysis", Crit Care Med., Editorial, vol. 35, No. 2 (2007) pp. 656-658.

Goodacre et al., "Prediction of Mortality Among Emergency Medical Admissions", Emerg Med J, vol. 23 (2006), pp. 372-375.

Greenhalgh, David G., "Hypoxic Pulmonary Vasoconstriction After Combined Burn and Inhalation Injury", Crit Care Med., Editorial, vol. 34, No. 5 (2006) pp. 1562-1563.

Groeneveld et al. "Catecholamines, Parasympathetic Stimuli, or Cortisol for Overwhelming Sepsis", Crit Care Med., Editorial, vol. 34, No. 5 (2006) pp. 1549-1550.

Hager, et al. "Customizing Lung-Protective Mechanical Ventilation Strategies", Crit Care Med., Editorial, vol. 34, No. 5 (2006) pp. 1554-1555.

Hart, G.K., "Editorial: Antecedents to Hospital Deaths: All in Good Time", Internal Medical Journal, vol. 31 (2001) pp. 321.

Herlitz et al., "Characteristics and Outcome Among Patients Suffering In-Hospital Cardiac Arrest in Monitored and Non-Monitored Areas", Resuscitation, vol. 48 (2001) pp. 125-135.

Herlitz et al., "Very High Survival Among Patients Defibrillated at an Early Stage After In-Hospital Ventricular Fibrillation on Wards With and Without Monitoring Facilities", Resuscitation, vol. 66 (2005) pp. 159-166.

Hillman et al., "Antecedents to Hospital Deaths", Internal Medical Journal, vol. 31 (2001) pp. 343-348.

Hillman et al., "Introduction of the Medical Emergency Team (MET) System: a Cluster-Randomised Controlled Trial", Lancet, vol. 365 (Jun. 18, 2005), pp. 2091-2097.

Hovda et al., "Oxidative Need and Oxidative Capacity Following Traumatic Brain Injury", Crit Care Med., Editorial, vol. 35, No. 2 (2007) pp. 663-664.

Hravnak, Marilyn, "Electronic Integrated Monitoring of Medical Emergency Team Calls to a Step Down Unit", This is Biosigns Presentation, (Jun. 2006).

Jacobs, et al., "Increasing Vigilance on the Medical/Surgical Floor to Improve Patient Safety", Journal of Advanced Nursing, vol. 57, No. 5 (2007) pp. 472-781.

Kause et al., "A Comparison of Antecedents to Cardiac Arrests, Deaths and Emergency Intensive Care Admissions in Australia and New Zealand, and the United Kingdom-the Academia Study", Resuscitation, vol. 62 (2004) pp. 275-282.

Knaus et al., "The APACHE Ill Prognostic System. Risk Prediction of Hospital Mortality for Critically Ill Hospitalized Adults", Chest, vol. 100 (1991) pp. 1619-1636.

Kramer et al. "Uniform Patient Assessment for Post-Acute Care", Division of Health Care Policy and Research, UCDHSC, Aurora, CO (Jan. 25, 2006), pp. 1-135.

Knoefel, Wolfram Trudo, "The Peritonitis Dilemma: Better Safe Than Sorry or Wait for the Cat to Jump", Crit Care Med., Editorial, vol. 35, No. 2 (2007) pp. 648-649.

Kruger et al., "Nonuse of Statins-A New Risk Factor for Infectious Death in Cardiovascular Patients", Crit Care Med., Editorial, vol. 35, No. 2 (2007) pp. 631-632.

Krumholz et al., "Randomized Trial of an Education and Support Intervention to Prevent Readmission of Patients with Heart Failure", JACC, vol. 39, No. 1 (Jan. 2, 2002) pp. 83-89.

Kucher et al., "Electronic Alerts to Prevent Venous Thromboembolism Among Hospitalized Patients", vol. 352, No. 10 (Mar. 10, 2005) pp. 969-977.

Landesberg et al., "Silent Myocardial Ischemia in the Noncoronary Intensive Care Unit: A New Frontier?", Crit Care Med., Editorial, vol. 35, No. 2 (2007) pp. 629-630.

Lemaire, Francois, "Low-Dose Perfluorocarbon: A Revival for Partial Liquid Ventilation", Crit Care Med., Editorial, vol. 35, No. 2 (2007) pp. 662-663.

Leonhardt, David, "Why Doctors So Often Get it Wrong", New York Times, (Feb. 22, 2006), available at http://www.nytimes.com/2006/02/22/business/22leonhardt.html?_r=&pagewanted=print&oref=slogin (last visited Jan. 14, 2008).

Lohr et al., "Smart Care Via a Mouse, but What Will it Cost?", New York Times, (Aug. 20, 2006), available at http://www.nytimes.com/2006/08/20/business/yourmoney/20info.html?_r=1&pagewanted=print&oref=slogin (last visited Jan. 14, 2008).

Luce, John. M., "Acknowledging our Mistakes", Crit Care Med., Editorial, vol. 34, No. 5 (2006) pp. 1575-1576.

Luna, Carlos M., "Modulating the Oral Colonization with Povidone-iodine Antiseptic: A New Approach for an Old Controversy", Crit Care Med., Editorial, vol. 34, No. 5 (2006) pp. 1572-1573.

Machado, Roberto F., "Nitric-Oxide Based Therapies in Sickle Cell Disease: The Evidence Continues to Mount", Crit Care Med., Editorial, vol. 35, No. 2 (2007) pp. 654-655.

Marini, John, J.. Lessons Learned: The Conditional Importance of High Positive End-Expiratory Pressure in Acute Respiratory Distress Syndrome, Crit Care Med., Editorial, vol. 34, No. 5 (2006) pp. 1540-1542.

Mimoz et al., "Prevention of Ventilator-Associated Pneumonia: Do Not Forget to Disinfect the Mouth", Crit Care Med., Editorial, vol. 35, No. 2 (2007) pp. 668-669.

Morgan et al., "An Early Warning Scoring System for Detecting Developing Critical Illness", Clinical Intensive Care, vol. 8, No. 2 (1997), pp. 11.

Morris, Alan H., MD "Extracorporeal Support and Patient Outcome: Credible Causality Remains Elusive", Crit Care Med., Editorial, vol. 34, No. 5 (2006) pp. 1551-1552.

Mundow, Anna, "A Cut Above?", Irish Times, (May 26, 2007).

Muhl, Heiko, "Controlling the Cytokine Storm y Insulin: Glycogen Synthase Kinase-3 as a Target in Systemic Inflammation", Crit Care Med., Editorial, vol. 34, No. 5 (2006) pp. 1567-1569.

Nasraway Stanley A., Jr., "'Search and Destroy' for Methicillin-Resistant *Staphylococcus aureus* in the Intensive Care Unit: Should This Now be the Standard of Care?", Crit Care Med., Editorial, vol. 35, No. 2 (2007) pp. 642-644.

Needham et al., "Critically Appraise Before you Believe: The Quality of Meta-Analyses in Critical Care Medicine", Crit Care Med., Editorial, vol. 35, No. 2 (2007) pp. 666-667.

Nozari, Ala, "Tuning Up the Compression and Applying the Choke for Better Horsepower in Resuscitation", Crit Care Med., Editorial, vol. 34, No. 5 (2006) pp. 1563-1564.

O'Rourke, Michael F., "Pressure Pulse Waveform Analysis in Critical Care", Crit Care Med., Editorial, vol. 34, No. 5 (2006) pp. 1569-1570.

Papadakos, Peter J., MD "The Long and Short of Sedation Practices: Daily Interruption or Bolus Sosing?", Crit Care Med., Editorial, vol. 34, No. 5 (2006) pp. 1544-1545.

Parienti et al., "Viral Pneumonia and Respiratory Sepsis: Association, Causation, or it Depends", Crit Care Med., Editorial, vol. 35, No. 2 (2007) pp. 639-640.

Parissopoulos et al., "Critical Care Outreach and the Use of Early Warning Scoring Systems; A Literature Review", Icus Nurs Web J, Issue 21, (Jan.-Mar. 2005), pp. 1-13.

Pear, Robert, "A.M.A. to Develop Measurement of Quality of Medical Care", New York Times, (Feb. 21, 2006), available at http://www.nytimes.com/2006/02/21/politics/21docs.html?pagewanted=print (last visited Jan. 14, 2008).

Plost et al., "Family Care in the Intensive Care Unit: The Golden Rule, Evidence, and Resources", Crit Care Med., Editorial, vol. 35, No. 2 (2007) pp. 669-670.

Rand Corporation, "An Argument for Electronic Records", New York Times, (Aug. 19, 2006).

Reilly et al., "Translating Clinical Research into Clinical Practice: Impact of Using Prediction Rules to Make Decisions", Ann Intern Med, vol. 144 (2006) pp. 201-209.

Rexius et al., "A Simple Score to Assess Mortality Risk in Patients Waiting for Coronary Artery Bypass Grafting", Ann Thorac Surg, vol. 81 (2006) pp. 577-582.

Sarasota's Guidelines for When to Call a Rapid Response Team (as seen by BJR posted on East Tower, floor 9), (Apr. 18, 2007).

Sheridan, Rob, "Reducing Blood Loss in Burn Care", Crit Care Med., Editorial, vol. 35, No. 2 (2007) pp. 665.

Sirio, Carl A. "Critical Care Performance Measurement: The Time has Come for All", Crit Care Med., Editorial, vol. 34, No. 5 (2006) pp. 1538-1539.

Southern et al., "Hospitals Care and Length of Stay in Patients Requiring Complex Discharge Planning and Close Clinical Monitoring", Arch Intern Med, vol. 167, No. 17 (Sep. 24, 2007) pp. 1869-1874.

Song et al., "Alveolar Hemostatis in Patients with Species-Specific Bacterial-Mediated Ventilator-Associated Pneumonia", Crit Care Med., Editorial, vol. 35, No. 2 (2007) pp. 652-653.

Sube et al., "Validation of a Modified Early Warning Score in Medical Admissions", Q J Med, vol. 94, (2001) pp. 521-526.

Tarassenko et al., "Integrated Monitoring and Analysis for Early Warning of Patient Deterioration", British Journal of Anesthesia, vol. 97, No. 1 (2006) pp. 64-68.

Teasdale et al., "Revisiting the Glasgow Coma Scale and Coma Score", Intensive Care Med, vol. 26 (2000) pp. 153-154.

Tirschwell, David, "Improved Prediction of Awakening or Nonawakening in Severe Anoxic Coma Using Tree-Based Classification", Crit Care Med., Editorial, vol. 34, No. 5 (2006) pp. 1573-1574.

Tsai, Amy G., "Can the Effects of Vasoactivity of Molecular Hemoglobin-Based Plasma Expanders be Ignored", Crit Care Med., Editorial, vol. 34, No. 5 (2006) pp. 1566-1567.

van der Voot, P.H.J., "Diagnostic and Scientific Dilemma: The Ischemic Bowel", Crit Care Med., Editorial, vol. 34, No. 5 (2006) pp. 1561-1562.

van der Voot, P.H.J., "The Incomplete Puzzle of Vasoactive Medication in (Abdominal) Sepsis", Crit Care Med., Editorial, vol. 34, No. 5 (2006) pp. 1565-1566.

Van Venrooij et al., "International Prostate Symptom Score and Quality of Life Assessment Versus Urodynamic Parameters in Men with Benign Prostatic Hyperplasia Symptoms", The Journal of Urology, vol. 153 (May 1995) pp. 1516-1519.

Wagner, Douglas P., Ph.D., "What Accounts for the Difference between Observed and Predicted?", Crit Care Med., Editorial, vol. 34, No. 5 (2006) pp. 1552-1553.

Wang et al., "Is Inter-Alpha Inhibitor Important in Sepsis", Crit Care Med., Editorial, vol. 35, No. 2 (2007) pp. 634-635.

Watkinson et al., "A Randomised Controlled Trial of the Effect of Continuous Electronic Physiological Monitoring on the Adverse Event Rate in High Risk Medical and Surgical Patients", Anesthesia, vol. 61 (2006) pp. 1031-1039.

Webster, Nigel R., "Monitoring the Critically Ill Patient", J.R. Coll. Surg. Edinb., vol. 44 (Dec. 1999) pp. 386-393.

Weisberg, Lawrence, S., "Sic Transit Acetylcysteine?", Crit Care Med., Editorial, vol. 35, No. 2 (2007) pp. 644-645.

Werdan, Karl, MD "Immunoglobulin Treatment in Sepsis—Is the Answer 'No'?", Crit Care Med., Editorial, vol. 34, No. 5 (2006) pp. 1542-1544.

Winters et al., "Rapid Response Systems: A Systematic Review", Crit Care Med, vol. 35, No. 5, (2007), pp. 1238-1243.

Winters et al., "Rapid Response Teams-Walk, Don't Run", JAMA, vol. 296, No. 13, (Oct. 4, 2006), pp. 1645-1647.

Young, G. Bryan, "Intensive Care Unit/Critical Illness Myopathy: Toward a Unifying Hypothesis", Crit Care Med., Editorial, vol. 35, No. 2 (2007) pp. 628-629.

Zimmerman et al., "Acute Physiology and Chronic Health Evaluation (APACHE) IV: Hospital Mortality Assessment for Today's Critically Ill Patients", Crit Care Med, vol. 3, No. 5 (2006) pp. 1297-1310.

PCT International Search Report based on PCT/US06/06467 dated Sep. 17, 2001.

PCT International Search Report based on PCT/US07/022054 dated Apr. 2, 2008.

Supplementary European Search Report based on PCT/US06/06467 dated Jul. 21, 2009.

Office Action in U.S. Appl. No. 11/362,450 mailed May 20, 2009.

International Search Report based on PCT/US06/06467 dated Sep. 14, 2007.

Braden, Barbara J., The Relationship Between Stress and Pressure Sore Formation *Ostomy/Wound Management* vol. 44, pp. 26S-37S (Mar. 1, 1992).

Marshall, John C. et al., Multiple Organ Dysfunction Score: A reliable descriptor of a complex clinical outcome *Critical Care Medicine*, vol. 23, No. 10, pp. 1638-1652 (Oct. 1, 1995).

Pollack, Murray M. et al. PRISM III: An updated Pediatric Risk of Mortality score *Critical Care Medicine*, vol. 24, No. 5, pp. 743-752 ( May 1, 1996).

International Search Report based on PCT/US09/061478 dated Dec. 10, 2009.

Office Action in U.S. Appl. No. 11/362,450 mailed Apr. 2, 2010.

Jones, "Glasgow Coma Scale," *The American Journal of Nursing*, 79(9), pp. 1551-1553 (Sep. 1979).

Rees, "Early Warning Scores," *Update in Anaesthesia, World Anaesthesia*, 17(10), pp. 30-33 (2003).

Reintam et al., "Gastrointestinal Failure in Intensive Care: A Retrospective Clinical Study in Three Different Intensive Care Units in Germany and Estonia," *BMC Gastroenterology*, 6(19), doi:10.1186/1471-230x-6-19 (Jun. 22, 2006).

Ryan et al., "Setting Standards for Assessment of Ward Patients at Risk of Deterioration," *British Journal of Nursing*, 13(20), pp. 1186-1190 (Nov. 2004).

Antman et al., "The TIMI Risk Score for Unstable Angina/Non-ST Elevation MI—A Method for Prognostication and Therapeutic Decision Making", JAMA, vol. 284, No. 7 (Aug. 16, 2000) pp. 835-842.

Egevad et al., "Prognostic Value of the Gleason Score in Prostate Cancer" BJU International, vol. 89, Issue 6 (Apr. 9, 2002) pp. 538-542.

Subbe et al., "Effect of Introducing the Modified Early Warning Score on Clinical Outcomes, Cardio-Pulmonary Arrests and Intensive Care Utilisation in Acute Medical Admissions" Anaesthesia, vol. 58, No. 8 (Jul. 14, 2003) pp. 797-802.

Office Action in U.S. Appl. No. 11/362,450 mailed Mar. 30, 2011.

* cited by examiner

SYSTEM AND METHOD FOR PROVIDING A HEALTH SCORE FOR A PATIENT

RELATED APPLICATIONS

This application claims the benefit of U.S. Provisional Application Ser. No. 60/851,835, filed on Oct. 13, 2006, the entirety of which is hereby incorporated herein by reference for the teachings therein.

FIELD OF THE INVENTION

The embodiments disclosed herein relate to a system and method for improving hospital patient care, and more particularly to a system and method for providing a continual measurement and display of each patient's health.

BACKGROUND

One of the major problems in delivery of effective medical treatment in hospitals is the quality and continuity of patient care. A typical patient, undergoing a serious procedure in a hospital, may easily see five or more physicians during a stay, and also many nurses and other supporting personnel. Maintaining a complete medical record for each patient ("charting") swallows huge amounts of nursing time without providing any guidance to the medical staff on how to improve the patient's care. The present state of the art in medical care within hospitals makes very little use of the medical record, which is so bulky and awkward that it can only be quickly perused by doctors on their rounds. Such reading of the chart makes it almost impossible to evaluate treatment modalities or to detect a patient's declining health in time for intervention (before a crisis).

During a week's hospital stay, each patient may see many doctors and many nurses. This makes it extremely difficult to provide continuity of care. Every different caregiver must understand the medical record to give the patient optimum care, but the form and content of present-day medical charting provides no help. Each subsequent physician, whether a consultant or a shift replacement, is ill-prepared by current methods to obtain a correct overall medical status of the patient, thus posing a danger to the continued care of the patient, particularly in the recovery stages after serious operations For example, an attending physician, while making rounds in a hospital, may stop in on a patient, see that the patient has good color and is sitting up in bed, and thusly satisfied, goes on to his next appointment. However, if that patient had been walking up and down the corridors two days ago, and now cannot get out of bed, there is a problem. The patient may be experiencing a major and potentially life-threatening complication.

The essence of this problem is that, although all the medical information is recorded, it is not easily understood. After just a few days in the hospital, a patient may have twenty or even one hundred pages in their hospital record, including physician progress reports, nursing evaluations, records of vital signs, test results, heart monitoring information, and so on. However, even if every doctor and nurse who saw the patient were fully aware of the material in this record, it would not be enough to allow for the best medical care because it is very difficult to detect trends in such voluminous data.

The result of this arrangement has been to allow a number of patients in recovery, post-operation or procedure, to deteriorate to the point of medical crisis before addressing their problems. This causes a serious drain to the resources of the hospital, and unnecessary pain and suffering, even death. It is particularly bothersome because many of the conditions that lead to such crises can easily be avoided if the failing condition of a patient were discovered hours or days earlier.

One thing that a few hospitals have done is to employ an Early Warning System (EWS) as a means for deciding whether a patient needs to be transferred to the ICU. Other hospitals have developed a Modified Early Warning System (MEWS). Both existing systems typically use a small number of factors such a pulse, blood pressure, temperature, and respiratory rate. For each factor, a partial score is given, and all of these are then tabulated into a total score, which in turn is expressed as a binary recommendation: whether or not to move the patient into the ICU; no other action is suggested, no other information is obtained.

Such systems determine a patient's need to be transferred to the ICU by providing an emergency alert. However, these systems do not provide assistance to the doctor or nurse in helping to anticipate and thereby avoid medical crises, nor are they helpful to the clinical researcher in evaluating the efficacy of procedures and treatments. They convey no health trend information. Also, they are limited in the number of factors analyzed and thus are not very sensitive to general health conditions.

For example, in the above-described example of a patient sitting up and alert in bed, this type of evaluation completely misses the patient's declining health. Because the patient still does have acceptable vital signs, he is not moved to the ICU, and neither the EWS, nor the MEWS, would generate an alert. However, if during the two previous days, this same patient had been walking around the hospital halls, but is now not able to rise from a bed, an important medical decline has happened, possibly one that will lead to a medical crises if not attended to, even though his major vital signs are still acceptable. Some embodiments of the present invention address these omissions, providing new continual, sensitive tools for improving medical care.

SUMMARY

Embodiments of the present invention may overcome the drawbacks associated with the prior art by providing a system and method for continually tracking the health of a patient in a hospital. Systems and methods for providing a Health Score for a patient are disclosed herein. According to aspects illustrated herein, there is provided a system for generating an indicator of a patient's health, the system including a data module receiving data relating to a patient's health, the data including subjective data, a conversion module generating an output from the data, the output representing the patient's health, and a display module displaying the output for a user to compare with the output analyze.

According to aspects illustrated herein, there is provided a method of providing a customizable system for generating an indicator of a patient's health, the method including providing a system including a data module receiving data relating to a patient's health, a conversion module generating an output determined using the data inputted into a first algorithm, the output representing the patient's health, and a display module displaying the output for a user to analyze, and customizing at least one of the first and a standard algorithms according to preferences of a user.

According to aspects illustrated herein, there is provided a method of generating indicators of a patient's health, the method including receiving data relating to a patient's health, generating an output from the data, the output representing the patient's health, displaying the output on a display module, and making a healthcare decision based on the output.

According to aspects illustrated herein, there is provided a system for generating an indicator of a patient's health, the system including a data module receiving data relating to a patient's health, the data including subjective data, a conversion module generating an output from the data, the output representing the patient's health, and a display module displaying the output and a standard output for a user to compare with the output.

In some embodiments, the data module may receive first data at a first time and second data at a second time, the conversion module may generate a first output representing the patient's health at the first time and a second output representing the patient's health at a second time, and the display module may plot the first and second outputs with respect to time as a patient's health graph and may plot standard first and second outputs with respect to time as a standard health graph.

According to aspects illustrated herein, there is provided a method of providing a customizable system for generating an indicator of a patient's health, the method including providing a system including a data module receiving data relating to a patient's health, a conversion module generating an output determined using the data inputted into a first algorithm, the output representing the patient's health, and a display module displaying the output and a standard output for a user to compare with the output, the standard output being generated by a second algorithm, and customizing at least one of the first and second algorithms according to preferences of a user.

According to aspects illustrated herein, there is provided a method of generating indicators of a patient's health, the method including receiving data relating to a patient's health, generating an output from the data, the output representing the patient's health, displaying the output on a display module, comparing the output with at least a second output, and making a healthcare decision based on the comparison.

Various embodiments provide certain advantages. Not all embodiments of the invention share the same advantages and those that do may not share them under all circumstances. Further features and advantages of the embodiments, as well as the structure of various embodiments are described in detail below with reference to the accompanying drawings.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
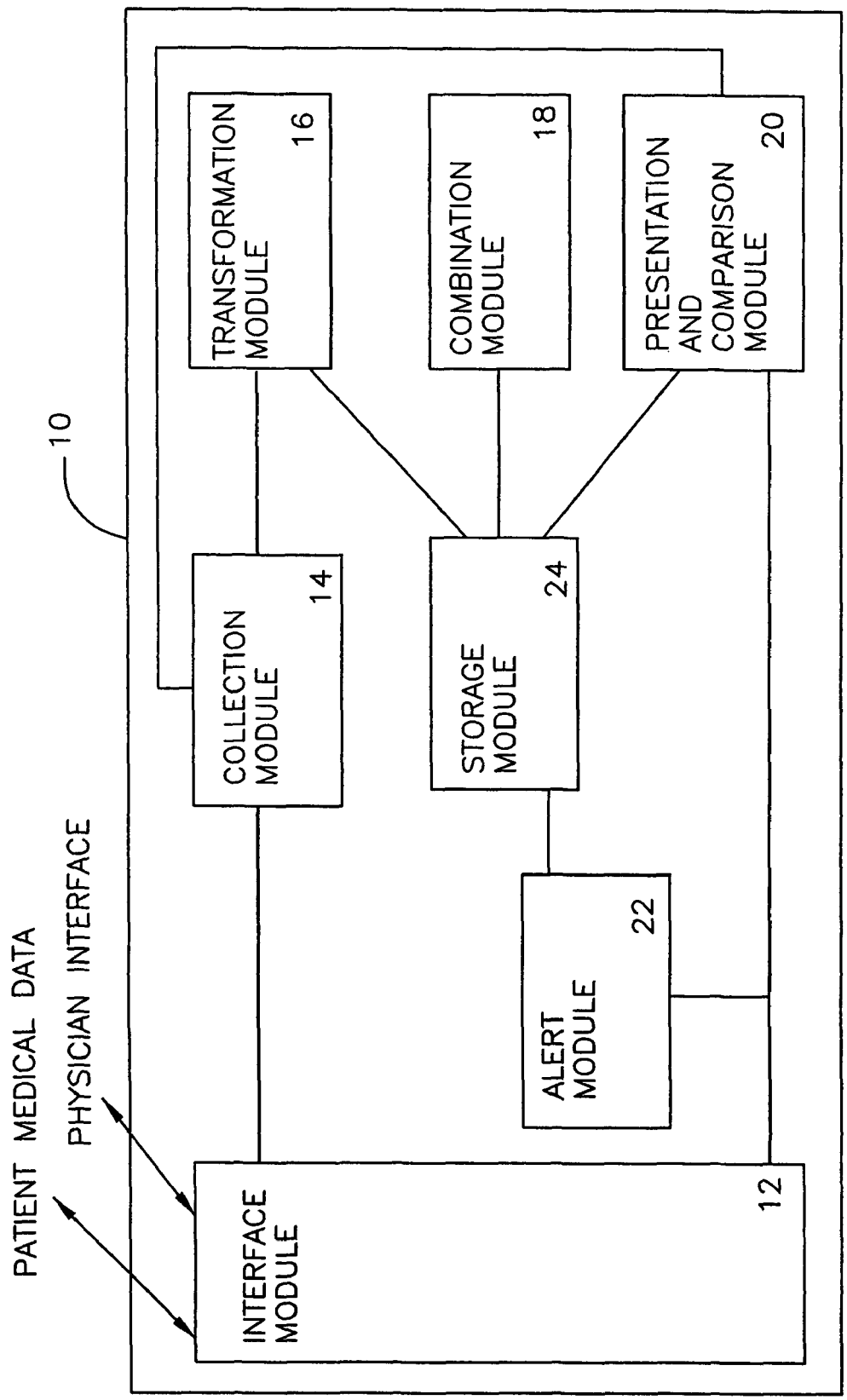
FIG. 1 depicts a logical diagram of the Health Score system, in accordance with an illustrative embodiment of the present invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Embodiments of the present invention provide a system and method for continually tracking the health of a patient in a hospital. At least some of the embodiments allow physicians, nurses and clinical researchers to provide more effective health care for each patient, especially those spending several days in a hospital. In addition or alternatively, at least some embodiments assist hospitals in avoiding errors and reducing crisis management by using the systems' capability to detect trends in a patient's health before the patient reaches a crisis point. Recognizing a decline soon enough to administer proper treatment may be a life-saving benefit. Embodiments of the system may give physicians and nurses a way in which to get the "big picture" of a patient's condition and absorb in a glance perhaps 100 pages of a patient's medical records. This deeper understanding, along with this new capability to detect health trends, short-term (over the space of hours) and/or long-term (over the space of days) may be important in delivery of effective medical care. Embodiments may enable a new field of scientific study, where medical and surgical treatments can be evaluated by the new measurements provided by embodiments of the present invention.

Embodiments of the present invention generate a new measurement of health, herein termed the patient "Health Score," which may be continually plotted and displayed to show each patient's medical progress during his hospital stay. The health of the patient may relate a patient's vitality and overall quality of life rather than simply being free from disease. Although a patient who has a terminal disease, such as cancer, may conventionally be considered to be in 'poor health'; however, if a cancer patient who only has a few months to live is playing ping pong for hours, he/she may be considered to be in good health, as the term is used herein. In comparison, a patient who entered the hospital to have a simple surgery, such as a tonsillectomy, may conventionally have been considered to be and will likely recover to be in 'excellent health.' However, while recovering, the tonsillectomy patient's vitality might be low and his/her change of dying in the near future could be much higher if a complication were to arise; thus, the patient may be considered to be in poor health, as the term is used herein. The health of a patient may relate to the patient's overall physical, mental, spiritual and social wellbeing and not merely the absence of disease or infirmity. Embodiments of the present invention may prove to be a vital aid for improving the quality and continuity of medical care.

To this end, embodiments of the present invention may provide systems for improving hospital patient care by generating a Health Score. The system may include an interface module for receiving incoming medical data from a patient, a transformation module for transforming the medical datum into a transformed Health Score value, and a combination module for combining the transformed Health Score values corresponding to each of the medical datum into a single Health Score. A presentation and/or comparison module displays the Health Score as a Health Score plot over a predetermined time frame, such that a user may identify health trends in a patient by evaluating said Health Score plot. The Health Score system is described in more detail below.

In addition to the features of the Heath Score and uses thereof, it is further contemplated that an exemplary use of such system may include the use of the Health Score (Health Score) to provide a panel of Health Score Charts, giving a nurse or doctor an overview as to the progress of many patients at one time, as is described further below.

In one embodiment, the Health Score may be used to predict the odds of a crisis within N number of hours. That is, for example, there is a 20% chance of a crisis in the next 12 hours. This information may be used to assign additional observation to particular patients, or if a crisis is judged to be imminent, a call may be initiated to a Rapid Response Team. Another use for the Health Score is to route doctor's rounds, so that walking instructions can be provided for a doctor doing rounds. This will allow a doctor to quickly move to patients requiring more attention first, and then proceed to less critical patients. A doctor or nurse may annotate a chart, such as adding a comment, for example "Breathing well," or a nurse could say "Tubes removed." Charts may also be annotated by adding special ICONS . . . for example, a walking man to show that the patient is now mobile. The name of the doctor who is treating the patient may also be added to the chart.

One way in which a crisis may be predicted is by comparing the individual patient's Health Score with a standard recovery curve. By tailoring the standard recovery curve to the patient, better results may be obtained. For example, one of the exemplary ways in which patients may be categorized is by DRG/ICD-9 grouping systems. DRG stands for a diagnostic related group and ICD-9 is the international classification of disease. Both of these are ways of categorizing patients based on what disease or ailment the patients have and are employed by insurance companies to figure out how much the insurance company should pay out for a particular policyholder in the hospital. For example, the standard recovery curve for someone having had elective rhinoplasty is likely to be very different from the standard recovery curve of someone who had a heart-lung transplant. If the rhinoplasty patient's health was declining, but the rhinoplasty patient's health was viewed in comparison with someone who had serious surgery, such as a heart-lung transplant, the decline might not be viewed as being significant, while in reality the rhinoplasty patient could be about to experience a cardiac or respiratory crisis. If the transplant patient's health is improving, but the patient's health is viewed in comparison with other patients who have had the same procedure and the recovery is much slower this could be an early indication of a complication. By comparing patients based on their disease, treatment/surgery, or affliction, the patient's Health Score may be better interpreted.

In some embodiments, ICD-9, which groups patients into thousands of detailed categories, normative data plots may be used, while in some embodiments DRG, which groups patients into about 500 categories, may be used, while in yet other embodiments, a combination of the two grouping systems may be used. Not all embodiments are intended to be limited in this respect and any disease grouping system or data may be employed to create a singular or combination standard recovery curve.

In some embodiments, creating the standard curve may entail reviewing graphs of all previous patients with the same DRG/IDC-9 code in a database and plotting them as one or more curves. The curve may be represented by an average curve, all of the individual patient's curves, a median curve, a top $25^{th}$ percentile and a bottom $25^{th}$ percentile, plus or minus some number of standard deviations thereby creating a normative recovery as well as upper and lower bounds, any combination of the foregoing or any other representative indicator as not all embodiments of the present invention are intended to be limited in this respect. By using these types of normative curves a doctor may be able to see that even if a patient is recovering, the patient might be recovering more slowly (too shallow a slope) than the average patient with a similar condition and this slower recovery might be cause for further investigation.

Not only may the grouping codes be useful in comparison with the Health Score, but the grouping codes may be utilized in generating a more accurate Health Score. In some embodiments, a user may modify the algorithm used to generate the Health Score based on the diagnosis or grouping code of the patient in order to have the Health Score more accurately reflect the patient's recovery Yet another exemplary use of the Heath Score arrangement is its use in predicting the length of stay for a patient or group of patients, sometimes termed ELOS (expected length of stay). Such an arrangement may be used to apply to a group of patients and therefore allowing a hospital to create a forward-looking resource plan, i.e. how many nurses are needed on a subsequent day of the week based on the current hospital population in a particular department. Some grouping codes, such as DRG, have ELOS times built into the grouping code, such that someone having a certain surgery will have an ELOS of a certain amount of time. For example, a patient having knee surgery may have an ELOS of 2.3 days and the hospital will be paid accordingly. However, if the patient actually takes 4.1 days to recover, the hospital may lose money or the patient may have to pay the difference, but if the patient if discharged after 1.5 days, the hospital may earn a profit.

In some embodiments, the life expectancy or mortality of a patient, such as the likelihood that a patient will die within the next 24 hours, may be predicted. For example, if a terminal patient is listed as DNR (do not resuscitate) or "keep patient comfortable," a family member may want to know the life expectancy of the terminal patient to plan for the inevitable death.

By comparing a patient's Health Score with a standard, many inferences may be drawn from the comparison. For example, in some embodiments, patients may be given a category, such as critical, critical but stable, serious, serious but stable, fair, and/or good. These categories may be words or terms, numbers (such as 1-5 or 1-100), colors (such as red, orange, yellow, or green), a made up system of categorizing, or any other system. In addition, the categories may be discrete, such as choosing one of four colors or may be continuous, such as choosing any number from one to 100.

By having patients categorized, administrative decisions and care priority can be determined accordingly. For example, in some embodiments, a nurse scheduling tool may be incorporated or separately determined which would allow shift nurses to see the conditions of all patients on the floor and assign nurses based on skill level, so that more experienced nurses have more critical patients and newer nurses have more stable patients. In some embodiments, the nurse scheduling tool may rank patients, for example, 1-10 and allocate patients to each nurse so that no nurse has a total patient rank of for example, more than 25 (e.g., two very critical patients of rank 10 and one fair but stable patient of rank 5, four fair but stable patients of ranks 5.2, 5.4, 5.7 and 6.1, or two serious patients of rank 8 and one serious but stable patient of rank 7.2). In some embodiments, the ELOS prediction may be incorporated into the nursing schedules, so that discharges may be predicted and the charge nurse may be able to know how many staff members may be required to work an upcoming shift. Similarly, these systems may be applied to routing a doctor's rounds, as described above.

In another possible arrangement, the Health Score may be used to determine priority and timing of the post-discharge "how are you doing" call. For example, patients leaving the hospital with favorable Heath Scores may be called in three days for a checkup, whereas patients with marginally acceptable Heath Scores may be called sooner.

The Heath Score as disclosed in the incorporated documents, and above may be fine tuned to each hospital in which it is implemented. Most hospitals have slight differences in procedures, standards, requirements and other elements of daily practice as compared to other hospitals and some embodiments of the present invention may be adapted to a specific hospital's preferences. In particular, when using subjective variables to produce a Health Score, as will be described further below, some hospitals may be more conservative in evaluating a patient's condition. For example, nurses at a first hospital may be taught that slightly grey skin is a reason to fail a skin assessment while nurses at a second hospital may be taught that a patient should pass a skin assessment until the skin is really grey. This difference may make average scores on the Health Score lower at the first hospital, which could mean that the predicted health of a patient would appear worse at the first hospital than at the second hospital. By adjusting the Health Score according to an individual hospital's procedures, the Health Score may be more accurate.

In some embodiments, the Heath Score may be used for evaluation purposes. For example, the Heath Score may be used to evaluate the performance of a particular doctor's or nurse's performance, or even of the hospital itself. It can also be used to evaluate a particular treatment by studying Heath Score charts of patients that underwent a particular treatment.

In addition to evaluation of doctors, the system may be used to compare effectiveness of medical treatments, compare the quality of care provided by different wards or hospitals, and compare the skill of healthcare providers by providing an objective assessment of a patient's health and response to various factors. In some embodiments, the algorithm may be customized after a patient's stay to further evaluate the care of the patient and compare the patient with other patients. For example, if two patients had the same diagnosis and received different treatments, a hospital or doctor may want to compare those two patients' recoveries. However, if one patient had a small drop in their Health Score due to an unrelated event, such as having an allergic reaction to topically applied medication, the algorithm may be adjusted to exclude a factor, such as a skin standard of the nursing assessment, from the Health Score of both patients, so that the two patients are still evaluated using the same algorithm, but the comparison is tailored to focus on the recovery from the treatments and exclude unrelated deviations.

In another embodiment, the Health Score chart shapes can be clustered to discover the "types" of patient health trajectories. General prototypical trajectories, or trajectories computed as a function of disease or procedure may be compared against actual Heath Score charts to determine how a particular patient is responding to treatment. Once a Health Score chart is assigned to such a prototypical trajectory, it may further indicate the likelihood of various outcomes. In some embodiments, this may be accomplished by using DRG/IRC-9 groupings, as discussed herein.

In another embodiment of the present invention, the Heath Score may be used as part of a remote monitoring service, where a remote health service provider can monitor the score of several patients and alert an on-site staff if there is an emergency. The Health Score can be refined using neural networks, or other analytical methods. The Health Score may be fed to a central data hub and be used to monitor for large scale trends in health problems, including a biological or chemical attack.

While in some embodiments an individual Health Score falling below a minimum mark or the change in Health Score or slope of the Health Scores falling below a minimum change may trigger an alarm or be interpreted by a healthcare provider as an indication of the patient's declining health, in some embodiments the change in slope or derivative of the slope of the Health Scores falling below a certain minimum may trigger an alarm or be interpreted by a healthcare provider as an indication of the patient's rapidly declining health. For example, if a patient is slightly declining and suddenly starts to decline at a much faster rate, this change in the acceleration of the slope may trigger an alarm. In some embodiments, the curvature of the Health Score plot may be provided, such as by a presentation and/or comparison module.

Many times a patient's health may be compromised in favor of conforming the patient's care to hospital standards. For example, many hospitals require their healthcare workers to take a patient's vital signs every 2-4 hours, which requires awakening patients during the night and often times not allowing them to complete a full sleep and enter deep sleep, which may be critical to a patient's recovery, and to draw blood from patients every day or two, which can be detrimental to an anemic or hemophiliac. If a patient has been recovering well and has an increasing Health Score, a healthcare worker may rely on the Health Score to determine whether or not a routine test or procedure may be skipped in order to allow the patient to better recover.

The system may include the ability to view a patient's prior hospital visits. In some embodiments, if a patient has a recurring condition, it may be preferable to view that patient's past Health Scores in addition to the present Health Score. In addition or alternatively, the graph may display a one or more Health Scores calculated using different inputs, such as a red line with circular data points for when the entry reflects nursing assessments, a blue line with square data points for blood work and/or a green line with triangular points for a chem panel. Differences in data source may be represented with unique icons or any other means of differentiating them, as not all embodiments are intended to be limited in these respects. In addition or alternatively, a doctor or healthcare provider may click on or hover over a point to access additional information, such as the data inputted to calculate the Health Score, an average reading, values from earlier in the patient's stay, or any other information.

In some embodiments of the present invention, a Health Score system 10 may be provided for generating and presenting a Health Score. The Health Score may be a medical reference "figure-of-merit" that is used by a health caretaker, such as a physician, nurse or other health attendant, to track the patient's health before, during or after a medical procedure or illness, in order to assist in preventing that patient from reaching a health crisis. When used in this manner, the Health Score chart enables the attending physicians and nurses to detect trends in the patient's health over time, particularly in evaluating post-operative recovery in the hospital. It also provides a statistically significant "outcome" for both clinical studies and retrospective studies of the relative efficacies among various surgical procedures or techniques, and among medical treatments and drugs.

In addition to short term intensive use of the Health Score system 10, a similar modified form may be used on a long term basis by regular general practitioners or other health care facilitates such as nursing homes. For example, as it stands, yearly physicals are usually accompanied by a series of medial measurements of the patient. Entering such data in Health Score system 10 may be useful in spotting long term declining health trends, even if none of the particular medical conditions have reached a crisis level.

To generate and present the Health Score, as illustrated in FIG. 1, system 10 may have an interface module 12, a collection module 14, a transformation module 16, a combination module 18, a presentation and/or comparison module 20, an alert module 22, and/or a storage module 24.

Interface module 12 may be configured to obtain or receive raw medical input, either directly from patient monitoring devices, or from attending physicians or nurses. Collection module 14 may collect the raw medical data from interface module 12, and further may collect additional material from storage module 24, including the patient's historical medical data as well as other required general medical data (optional statistics). In some embodiments, the raw medical data may be transmitted to transformation module 16, and the stored and historical medical data may be sent to presentation and/or comparison module 20. In some embodiments, the medical and historical data may be sent to the transformation module 16 and/or the presentation and/or comparison module 20.

Transformation module 16 may receive incoming raw medical data and may convert this data into a usable format for generating the patient's Health Score. Transformation module 16 may convert raw medical data into a form that will allow different types of data to be combined, such as a scaled number. The transformed data may then be sent to combination module 18, which in turn may generate a patient's Health Score, using a predetermined algorithm. The combination module 18 may combine the transformed Health Score values corresponding to the medical data into a single Health Score, such as by adding the scaled numbers and applying a predetermined algorithm to the sum of the scaled numbers to generate a Health Score.

Presentation and/or comparison module 20 may receive the calculated Health Score and may prepare a Health Score chart 100, plotting the patient's Health Score as a function of time. In some embodiments, the presentation and/or comparison module 20 may display the Health Score as a Health Score plot over a predetermined time frame, such that a user may identify health trends in a patient by evaluating the Health Score Plot. Alert module 22, may generate an alarm for the attending physicians and nurses when a problem is detected with a patient's Health Score chart 100. An alert may be activated for such problems when the Health Score of a patient descends below an acceptable threshold, determined in advance by system 10 or set by the attending physician, or if a downward trend is detected. Storage module 24 may be configured to store and retrieve Health Score information at various times during the Health Score generation and presentation procedure.

It is understood that the above list of modules is intended only as a sample of the logical organization of modules within system 10. For example, many of the modules may be combined with one another or subdivided and separated according to their function. In some embodiments, a data module may act as a collection for all data, both as inputted into an interface module and as stored in a storage module, a conversion module may transform and combine the data using an algorithm and creating an output, and a display module may present and compare the output as well as alert a healthcare provider to a potential issues. Any similar Health Score system, employing similar logical modules to obtain a Health Score is also within the contemplation of the present invention.

Furthermore, it is noted that the modules of system 10, illustrated in FIG. 1, are to show their logical relationship to one another. However, this is not intended to limit the physical construction of such a system. For example, system 10 may be employed on a single larger computer or on a series of smaller computers, possibly with different components residing within different geographical locations, such as the use of an off-site storage module 24. Any health care system 10 may employ similar modules to generate a Health Score alert, as not all embodiments of the present invention are intended to be limited in this manner.

Figure 2:
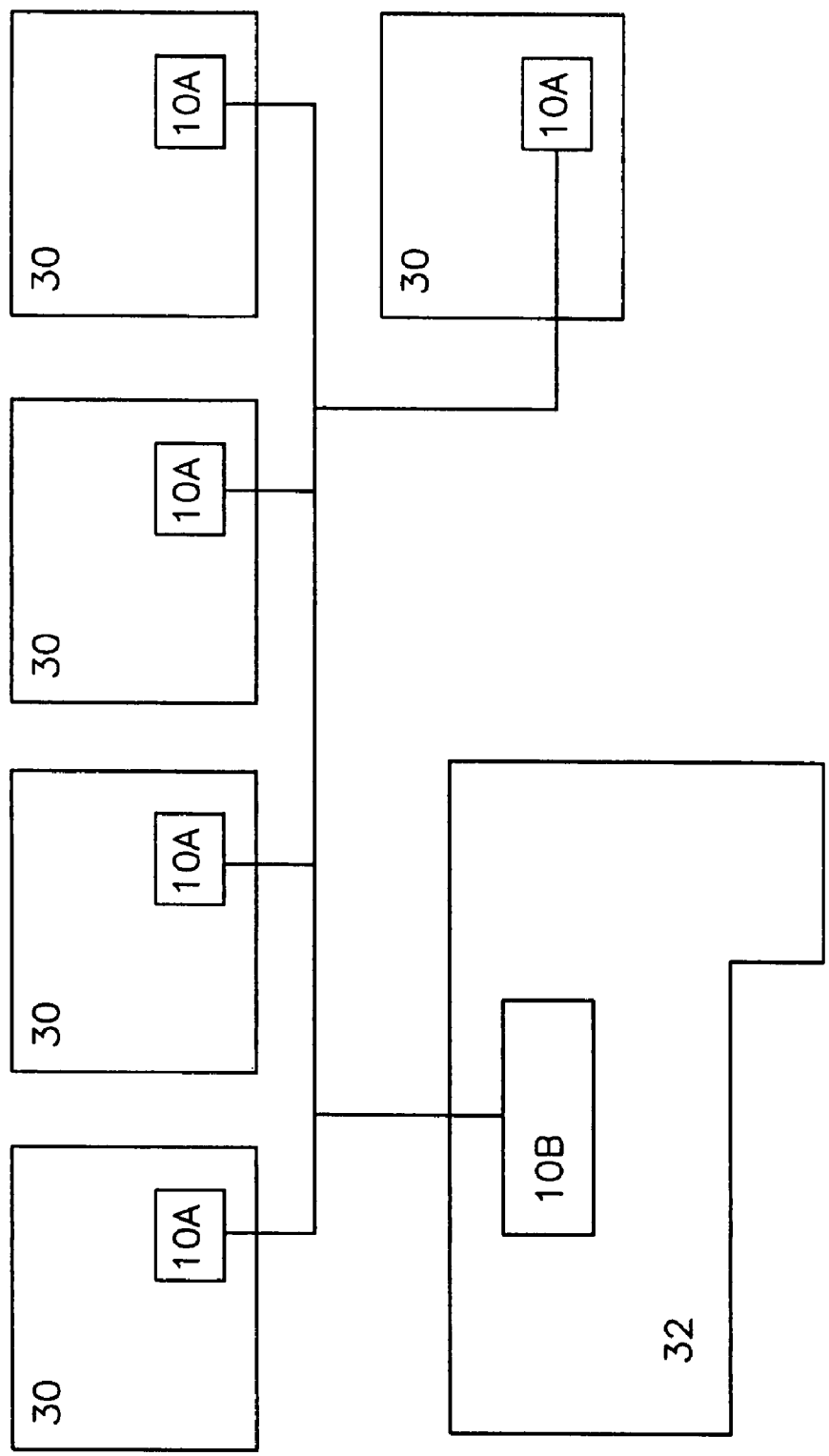
FIG. 2 depicts an installation arrangement of the Health Score system, in accordance with an illustrative embodiment of the present invention.

FIG. 2 depicts an exemplary embodiment of an arrangement for system 10, showing five patient recovery rooms 30, in a typical hospital with a central nursing station 32 that is monitored 24 hours a day. System 10 may have a local terminal 10A in each of the five patient rooms 30 and a main terminal 10B at nursing station 32.

Figure 3:
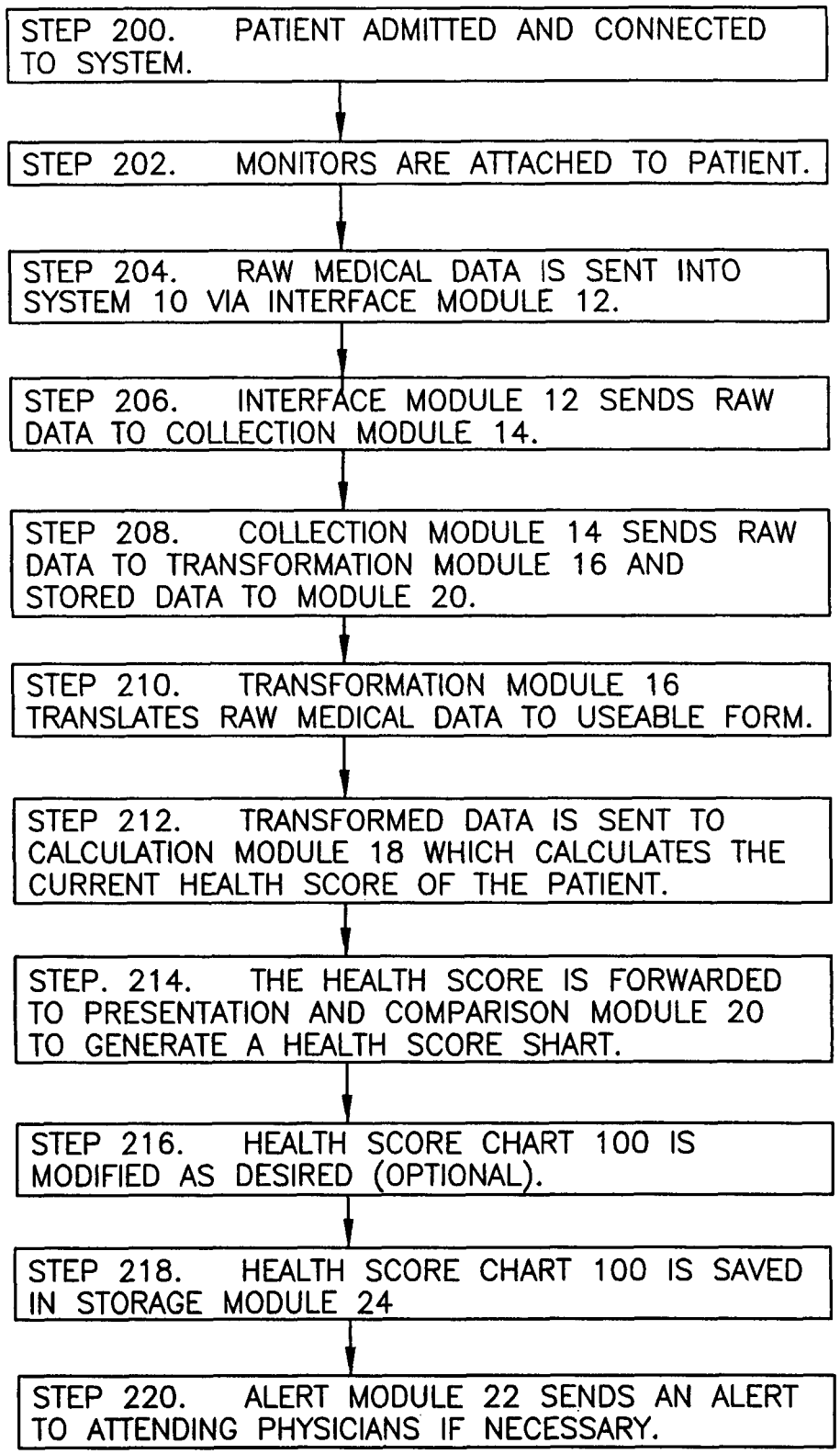
FIG. 3 depicts a flow chart of the generation of a Health Score chart, in accordance with an illustrative embodiment of the present invention.

FIG. 3 is a flow chart outlining the process for generating and presenting a patient's Health Score via system 10. In step 200, a patient may be admitted for a particular illness or surgical procedure and is subsequently connected to system 10. At step 202, various medical devices/monitors for obtaining the pertinent raw medical data are attached to the patient, such as blood pressure monitors, heart rate monitors, etc.

At step 204, interface module 12 may begin obtaining the pertinent raw medical data about the patient and imports this data into system 10. Some data may be obtained directly from the attached medical devices or from electronic medical records. Other data may be entered into the system by an attending physician or nurse. At step 206, this data may be sent to collection module 14. At step 208, collection module 14 may further obtain any necessary past medical data, most importantly the past Health Scores of the same patient. The raw data may be transmitted to transformation module 16, and the historical data is sent to presentation and/or comparison module 20.

Next, at step 210, transformation module 16 may transform the raw patient medical data into a usable format, so that all of the disparate forms of medical data can readily be compiled with one another. At step 212, the transformed medical data may be sent to combination module 18, which converts that raw transformed medical data into a Health Score using a predetermined algorithm. At step 214, the Health Score may be transmitted to presentation and/or comparison module 20, which uses the current Health Score, as well as historical data from storage module 24 (past Health Scores), to generate a Health Score chart 100.

Figure 4:
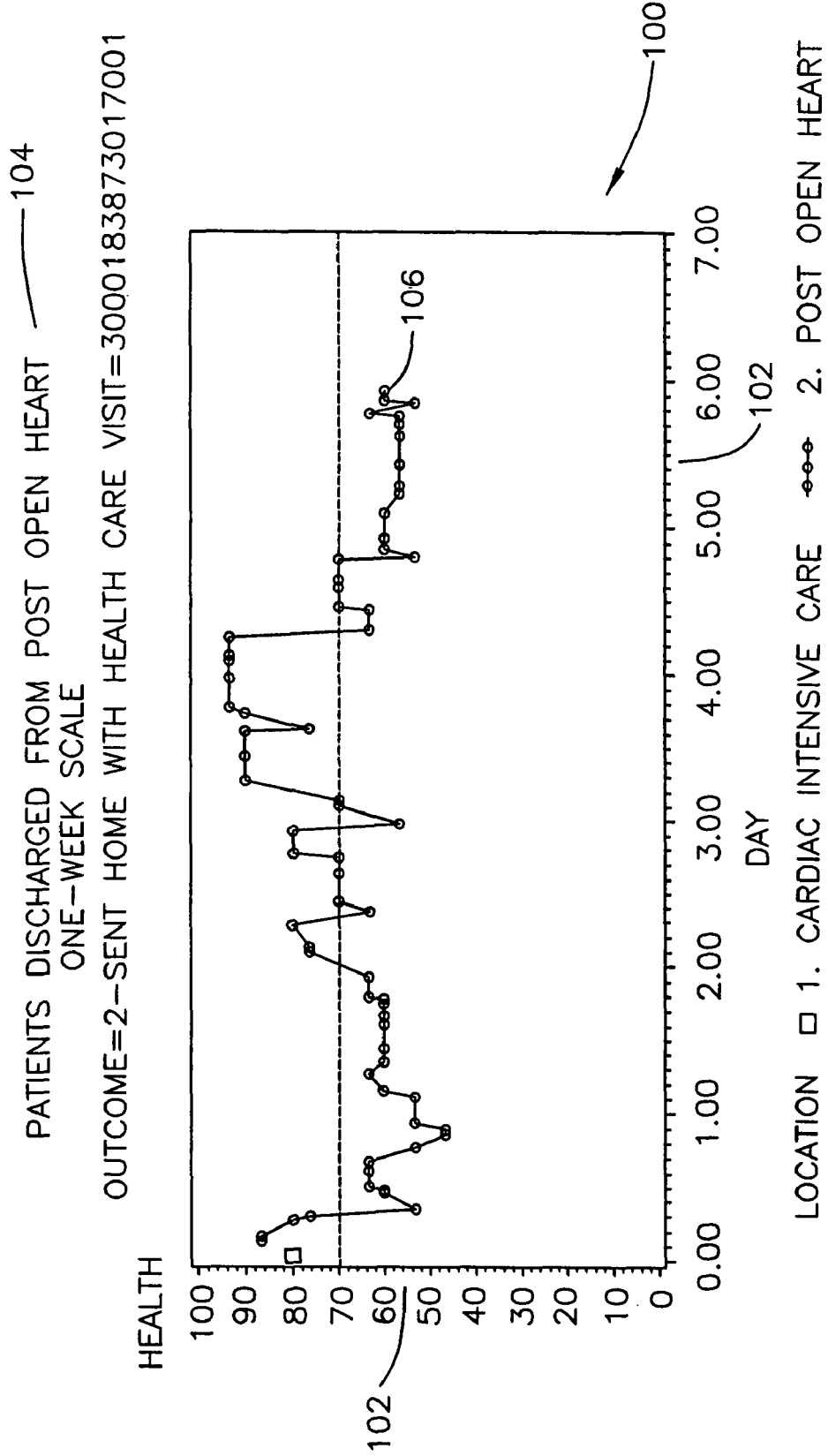
FIG. 4 depicts a sample Health Score chart, in accordance with an illustrative embodiment of the present invention.

A sample Health Score chart 100 is shown in FIG. 4, plotting a patient's Health Score, calculated by system 10 as a function of time. Chart 100 includes scale markings 102 and label material 104 and a Health Score plot 106. This chart 100 shows a sample Health Score plot 106 for a patient recovering from open-heart surgery, for 6 days. Initially the recovery was going well, but at approximately the beginning of the fourth day, health deteriorated. A more detailed description of the contents and evaluation of a Health Score chart 100 is included below.

At step 216, after Health Score chart 100 has been generated, presentation and/or comparison module 20 may modify and display the Health Score chart 100 to healthcare providers, via interface module 12 of system 10. At step 218, presentation and/or comparison module may further save any necessary information to storage module 24.

Finally at step 220, if the Health Score, according to plot 106, falls below a predetermined threshold, alert module 22 may inform the healthcare providers, either through interface module 12 or via some other alarm, that the patient is in need of attention.

It is noted that the above list of steps for generating Health Score chart 100 via system 10 is intended only to show an exemplary step-by-step process. For example, several of the steps may be combined with one another or possibly one step may be divided into a number of subroutines. Any similar process using steps to create a Health Score chart on a similar system is also with in the contemplation of the present invention.

Turning now to a more detailed description of the various modules of system 10, interface module 12 may receive raw medical data input at step 204, and transmits it to the various collection and processing modules 14, 16, 18, 20, 22 and 24 of system 10, at step 206. Typically, the input may include any number of the medical statistics that are used to generate the Health Score produced by system 10. Interface module 12 of system 10 may be as simple as a keyboard and monitor, used for manual entry of patient data. Furthermore, it may additionally include a set of automated electrical instruments such as pulse clips, automated blood pressure devices, blood oxygen measuring devices, fluid monitoring devices or any other standard medical measuring device, attached either by wire or remotely to interface module 12.

In addition to providing an interface for receiving medical data on the patients, interface module 12 may also be configured to present a means for users, such as doctors or nurses, to update, modify or review the patient's Health Score at step 216. Furthermore, interface module 12 may also be employed by alert module 22 at step 220 to alert the healthcare providers that alert module 22 has detected a threshold breach, which is explained in greater detail below Collection module 14 may be coupled to interface module 12 for receiving the various raw patient data at step 206. Collection module 14 may accept this data from various ports, including interface module 12 as well as other programs, such as electronic medical records (EMR), and stores this data in storage module 24. Thus, in addition to the raw physical patient data and physician/nurse input obtained from interface module 12, collection module 14 may further collect and organizes all of the data necessary to generate and maintain the Health Score chart 100 of the patient, including collecting historical data, performed at step 208.

In some embodiments of generating a Health Score chart 100, the patient data that may be collected by collection module 14 of system 10 may include both subjective and objective data. Although objective data has been used in the past to generate a single number representing a patient's health, subjective data, such as nursing assessments, may be very significant in predicting the health of a patient. Subjective data may include variables, which may require human evaluation or assessment, rather than collecting a numerical value, such as blood pressure, heart rate, and other measurable factors. On some embodiments, subjective data includes information commonly collected in nursing assessments. Examples of subjective data may include standards which are determined by a nurse after assessing a variety of factors in a category, such as cardiac standard (which may be include factors, such as pulse rate in beats per minute, warmth and dryness of ski, blood pressure, and/or symptoms of hypotension), food/nutrition standard ((which may be include factors, such as ability to chew and/or swallow, manual dexterity, and/or consumption of daily diet as ordered, observed or stated), gastrointestinal standard (which may be include factors, such as feel and appearance of the abdomen, bowel sounds, nausea or vomiting, continence and/or bowel patterns), genitourinary standards (which may be include factors, such as voids, continence, urine color and/or smell as observed or stated, and/or urinary catheter), musculoskeletal standards (which may be include factors, such as ability to move all extremities independently and/or perform functional activities as observed or stated, including use of assistive devices), neurological standards (which may be include factors, such as alertness, orientation to persons, place, time and situation and/or speech coherence), pain standard (which may be include factors, such as pain/VAS level and/or chronic pain management), peripheral vascular standard (which may be include factors, such as normal appearance and feel (e.g., warm and pink) of extremities, capillary refill, peripheral pulses, edema, numbness and/or tingling), psycho-social standard (which may be include factors, such as appropriateness of behavior to situation, expressed concerns and fears being addressed and/or support system), respiratory standard (which may be include factors, such as respirations at rest, bilateral breath sounds, nail beds and mucous membranes, and/or look and feel of sputum), safety/fall risk standard (which may be include factors, such as risk of patient to self and/or others), and/or skin/tissue standard (which may be include factors, such as skin CD&I, reddened areas, alertness, cooperation and ability to reposition self independently, and/or Braden scale). In some embodiments any or all of the above standards can be determined by a nurse using a pass/fail system. Even though these standards may be binary assessments, the transition from passing a standard to failing a standard can be very predictive in indicating the health of a patient. For example, if a patient moves from failing two standards, to failing five standards, to failing 7 standards, the patient may be going through a very serious decline in health, even if the patient's vital signs are relatively normal or not changing.

This information can be collected in any way, such as a nurse filling out a checklist on a clipboard, entering the data directly into a computer, PDA, a handheld electronic device or any other device, as not all embodiments are intended to be limited in this respect. In additional or alternatively, these determinations may be made by means other than healthcare workers, such as by a smart bed or another device which can provide an electronic assessment.

In some embodiments, additional data from a healthcare provider's notes may be incorporated as data. For example, a patient may have passed the respiratory standard of a nursing assessment, but the nurse may have indicated a notation of "diminished breathing capacity." This note may be incorporated into the nursing assessment analysis or as a separate variable as not all embodiments of the present invention are intended to be limited in this respect.

In some embodiments of the present invention, a single term in the Health Score formula may contain multiple medical data inputs. For example, as noted in the above incorporated discussions of Heath Score various medical readings (e.g. blood pressure, heart rate etc. . . . ) are each transformed into a particular number which are combined to form the plotted Heath Score. It is understood however, the multiple medical data inputs may be combined before being transformed, such that the transformed number used for forming a portion of the Heath Score, may be a combination of multiple health readings. For example, systolic and diastolic blood pressure may be combined into a single number before being transformed for use in the Heath Score. Factors used in determining the Health Score may include objective and subjective factors, such as diastolic blood pressure, systolic blood pressure, temperature, pulse, respiration rate, a pain score, weight, skin breakdown score, EKG pattern, and a set of nursing assessments, as described above. Thus, collection module 14 may obtain both past and present data necessary for the patient on each of the categories to form Health Score chart 100. Other inputs into the system may include weight, height, body mass index, or any other variables as not all embodiments of the present invention are intended to be limited in this manner Transformation module 16 may be configured to transform each of the pieces of medical data obtained from collection module 14 into a numerical quantity at step 210. The transformation performed by module 16 may include any number of mathematical or logical operations. Transformations may also take multiple inputs to produce a single transformed output. Multiple inputs may include historical data for this patient or for any given class of patients. For example, if the patient's pulse is greater then one standard deviation above that expected for a certain group of patients at this stage of their recovery, then the value of "High Pulse" is one, otherwise it is zero. An example of a transformation for diastolic blood pressure (TDBP) would be:

if diastolic blood pressure (DBP)<50, then TDBP=2;
if DBP>50 and DBP<90, then TDBP=0;
if DBP>89 and DBP<100, then TDBP=1;
if DBP>99 then, TDBP=2.

In this case, either very low values of diastolic blood pressure (less than 50), or high values of diastolic blood pressure (greater than 99), are considered dangerous.

Another example of a transformation may be for a nursing assessment. For example, if the respiration assessment equals "met standards" then the transformed respiration rate equals zero. If the nursing assessment for respiration equals "did not meet standards" then the transformed respiration rate equals one.

Thus, transformation module 16, after receiving raw data from collection module 14, may process the data and transforms them into numbers for use in generating a Health Score for the patient.

The following serves as an exemplary embodiment of a list of typical conversions of raw medical data into numerical form ("transformed numbers") by transformation module 16, for use by system 10 in developing a patient Health Score:

if diastolic blood pressure<50 then Transformed Diastolic BP=2
diastolic between 50 and 89, then . . . 0
diastolic between 90 and 99, then . . . 1
diastolic>99, then . . . 2
all nursing assessments . . . Met=0 . . . or Not Met=1
multiply cardiac, neurological, pain, peripheral vascular, psychosocial, respiratory and skin/tissue assessments by 2
if Braden score<18, then . . . 1
if Braden score greater or equal to 18, then . . . 0
if systolic blood pressure<70, then . . . 3
if systolic>69 and <81, then . . . 2
if systolic>80 and less than 101, then . . . 1
if systolic>100 and <200, then . . . 0
if systolic>199, then . . . 2
if heart rate<40, then . . . 2
if heart rate>39 and <51, then . . . 1
if heart rate>50 and <101, then . . . 0
if heart rate>100 and <11, then . . . 1
if heart rate>110 and <130, then . . . 2
if heart rate>129, then . . . 3
if respiration<9, then . . . 2
if respiration>8 and <15, then . . . 0
if respiration>14 and <21, then . . . 1
if respiration>20 and <30, then . . . 2
if respiration>29, than . . . 3
if temperature<95, then . . . 2
if temperature>94 and <101.1, then . . . 0
if temperature greater or equal to 101.1, then . . . 2
If the monitored heart pattern is "atrial fibrillation", "sinus rhythm", "sinus tachycardia" or "paced" then . . . 1
If the monitored heart pattern is "sinus bradycardia" then . . . 2
If the monitored heart pattern is "atrial flutter" OR "heart block" then . . . 3
If the monitored heart pattern is "junctional rhythm" then . . . 4
If the monitored heart pattern is "ventricular tachycardia" then . . . 5
Or if the monitored heart pattern is "ventricular fibrillation" then . . . 5.

These conversions of patient data into numbers are done solely for the purpose of example. It is understood that any conversion of raw medical data into a useable form for further calculation within the context of system 10 is within the contemplation of the present invention.

The above conversions of medical data into scaled numbers is geared to assessment of negative factors. However, it is understood that positive assessments may be included too, resulting in "negative" scaled numbers, that would show a positive affect on the Health Score. For example, transformation module 16 may give a negative scaled number in the event that heart rate or lung capacity or other such medical data is not only OK, but is in fact at an ideal state.

Combination module 18 may be configured to take the transformed quantities from transformation module 16, apply weighting modifiers, and to combine them, and then to scale them onto a range, such as a score between 0 and 100, at step 212. This score, generated by combination module 18, is based on the various health factors measured and transformed above, the resulting score being a relative overall Health Score of the patient being monitored.

An example of a combination Health Score generated by combination module 18, using the "transformed numbers" (as described above) generated by transformation module 16 of system 10, may be:

"Health Sum"=Diastolic Blood Pressure+Temperature+Respiration+Systolic Blood Pressure+Heart Rate+Braden Score+Cardiac Assessment+Food Assessment+Gastrointestinal Assessment+Genitourinary Assessment+Heart Rhythm+Musculoskeletal Assessment+Neurological Assessment+Pain Score+Pain         PART 1

Assessment+Peripheral Vascular Assessment+Psycho-Sociological+Respiratory Assessment+Safety/Fall Assessment+Skin/Tissue Assessment Health Score=100*(30−"Health Sum")/30    PART 2

Based upon the above formulae, a sample calculation of a patient's Health Score could be performed by transformation module 16 and combination module 18, if the collection module 14 of system 10 found the following raw medical data:

Diastolic Blood Pressure of 95=1
Negative nursing cardiac assessment=2
Negative nursing respiratory assessment=2
Braden Score of 18=0
Systolic Blood Pressure of 202=1
Heart Rate of 100=1
Respiration Rate of 14=0
Temperature of 98=0
Heart Rhythm of sinus bradycardia=2
"Health Sum"=(totaling of all above)=9

Health Score=100*(30−"Health Sum")/30=100*(30−9)30=70

Such transformations and calculations are intended only to be a simple example of determining a Health Score, as performed by system 10. However, it is in no way intended to limit the possible methods of calculating the score. For example, not all measured raw medical data need to be incorporated into a Health Score. The attending physician may wish to generate the score using only limited data to prevent non-essential medical data from significantly altering the Health Score.

Another example would be to include the use of weighting factors (2 times, 3 times, etc.) that can be added or multiplied to certain transformed numbers, such as the respiratory factors, when a particular patient is recovering from a lung-based ailment such as pneumonia. Likewise, similar weighting factors can be added to the transformed scores of heart rate, heart rhythm, systolic and diastolic pressure for patients with heart ailments. It is understood that any number of modifications introduced into a similar combination module 18 within a similar system 10 for generating a Health Score is within the contemplation of the present invention.

Presentation and/or comparison module 20 of system 10 may be configured to import the various data components compiled by combination module 18 and to create a Health Score chart 100 for the patient at step 214, and may display it via interface module 12 of system 10, or on an existing medical information system, such as the hospital's pre-existing computer system. In some embodiments, the presentation and/or comparison module 20 may include a statistical reference curve on said Heath Score plot, so that the Health Score may be easily compared to an average patient with similar conditions and circumstances. In some embodiments, the presentation and/or comparison module 20 may supply principal corresponding measurements of direct raw medical data on said Heath Score chart, may provide a smoothed Heath Score curve, alongside said Heath Score plot that provides a running average of the Health Score plot over time and/or may supply the curvature of a smoothed Health Score plot.

As discussed above, FIG. 4 illustrates a sample Health Score chart 100 generated by system 10 using the above-described modules. Additional functions of comparison module 20 are shown below which edit, modify or otherwise present various versions of Health Score chart 100, performed by system 10 at step 216.

Health Score chart 100 may be for displaying the Health Score of a patient at particular times, and more importantly, may be for detecting trends in a patient's health. Thus, Health Score chart 100 may include a number of Health Score assessments taken frequently, both at periodic (e.g. every 15 minutes, or every 3 hours), or at irregular intervals. This generates the Health Score chart 106 as shown in FIG. 4, plotting the patient's Health Score versus time as set by scales 102.

For example in FIG. 4, the Health Score of the patient may be computed ten times a day, approximately every 2 hours over the course of the six-day post-operative stay. During the first four days, the patient progressed from an average Health Score in the low 60s to the high 80s. But shortly thereafter, at the beginning of the fourth day, the patient's score began to decline back into the 60s range.

It is at this particular moment, at the beginning of the fourth day, that the Health Score chart 100 can prove to be a critical tool for medical care. If an attending physician were to see this patient at the end of day 4 without the Health Score chart, the patient's vital statistics would show a person of decent physical health. This corresponds to the score of 70 on the health chart, which is about average health during a post-operation recovery, according to this example. Thus without the chart 100, the patient would exhibit decent health, and the attending physician would have to rely his own quick perusal of the patient's medical records.

However, with the Health Score chart 100 available, it would be obvious to a physician or nurse that something is going wrong with the patient at the end of day 4. This is a critical time for the patient, because immediate treatment may prevent a crisis. The new information conveyed by chart 100, beyond what is normally available (that the patient is currently in an acceptable state), is that: less than 1 day ago, this patient was in a much better general state of health and is currently in a state of declining health. Thus by intervening in the situation right at the beginning of day 5, the doctors were able to stabilize the patient without further significant decline, so that he could be released from the hospital at the end of day 6.

Figure 5:
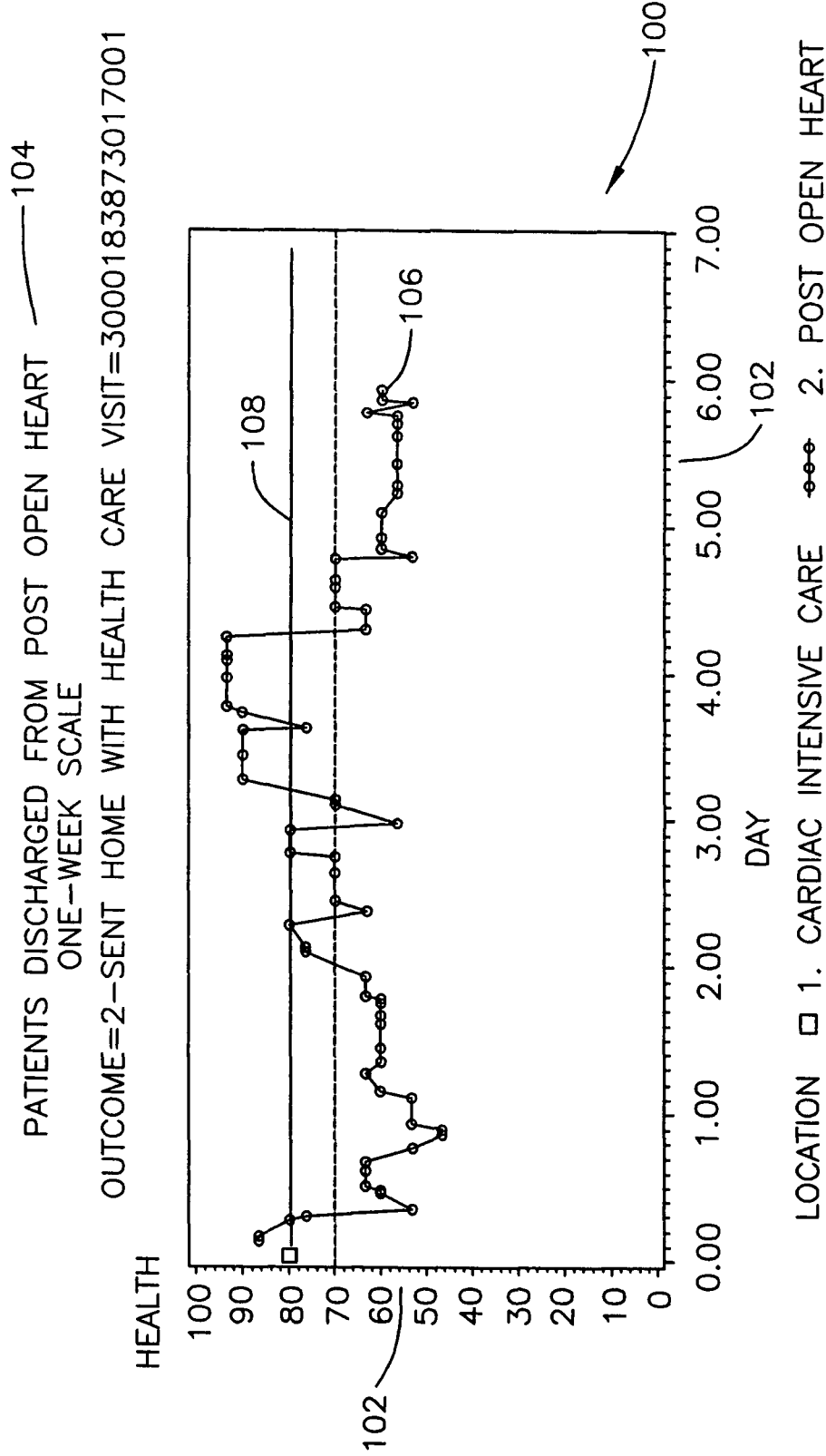
FIG. 5 depicts a sample Health Score chart with pre-operation information, in accordance with an illustrative embodiment of the present invention.

Comparison module 20 may be used to generate and present pre-operation reference curves. Information from pre-operation 108 may be posted on the patient's Health Score chart 100 so as to give additional context to their condition. For example, before an operation, the patient may have exhibited a Health Score of 50. After the operation, the doctors may expect the patient to be significantly better. Since before the operation he had a Health Score of 75, we expect that, although he will go through some difficult periods during recovery, he will get back to 75 within a week. This acts as a baseline reference, to help better personalize the chart 100 to each patient. FIG. 5 shows an example of pre-operation Health Score information 108, included on a typical Health Score chart 100, with a pre-operation Health Score of 80.

Statistical reference curves 110 may also be added to Health Score chart by comparison module 20. For example, when such information is available, statistically computed average patient Health Score trajectories, for each specific procedure and initial patient condition, may be included on chart 100 next to the Health Score plot 106. This information may be stored in a storage module 24, and may be imported into comparison module 20 by collection module 14. Statistical reference curves 110 may include linear information with standard deviation error bars or transformed values. If the patient is below expectation by a certain number of standard deviations, the system generates an alert using alert module 22, as discussed below.

Figure 6:
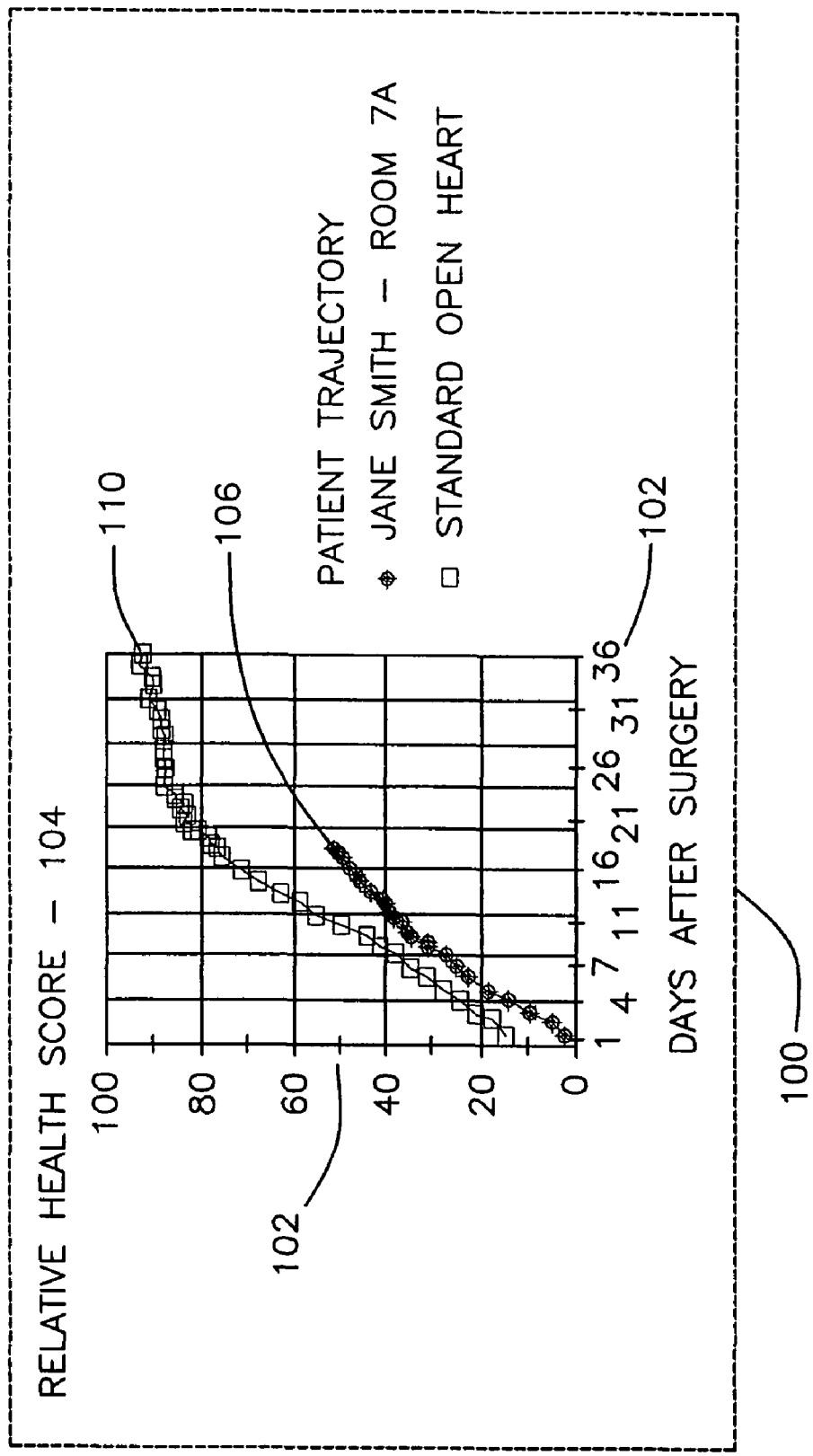
FIG. 6 depicts a sample Health Score chart with statistical reference curves, in accordance with an illustrative embodiment of the present invention.

For example, in FIG. 6, on the Health Score chart 100, the line labeled "Standard Open Heart" may be a statistical reference curve 110 of the average recovery of an open-heart surgery patient of age 80. The Health Score plot 106 labeled "Jane Smith—Room 7A" is the actual Health Score representation of the recovery of Jane Smith. One sees that although Ms. Smith has steadily improved since her operation, for the last several days she has improved at a much slower rate than would be expected when compared to average (past) patients of the same age undergoing a similar procedure. Statistical reference curves 110 can be compiled from current patients or an evaluation of past patients by using their records to generate Health Score histories.

Further subdivisions can also be made for such statistical reference curves. For example, instead of having a single reference curve 110 for average open-heart patients of age 80, it can be further broken down by gender, and even further modified as to a patient's initial condition by using only patients with similar Health Scores at the time of admission into the hospital.

Figure 7:
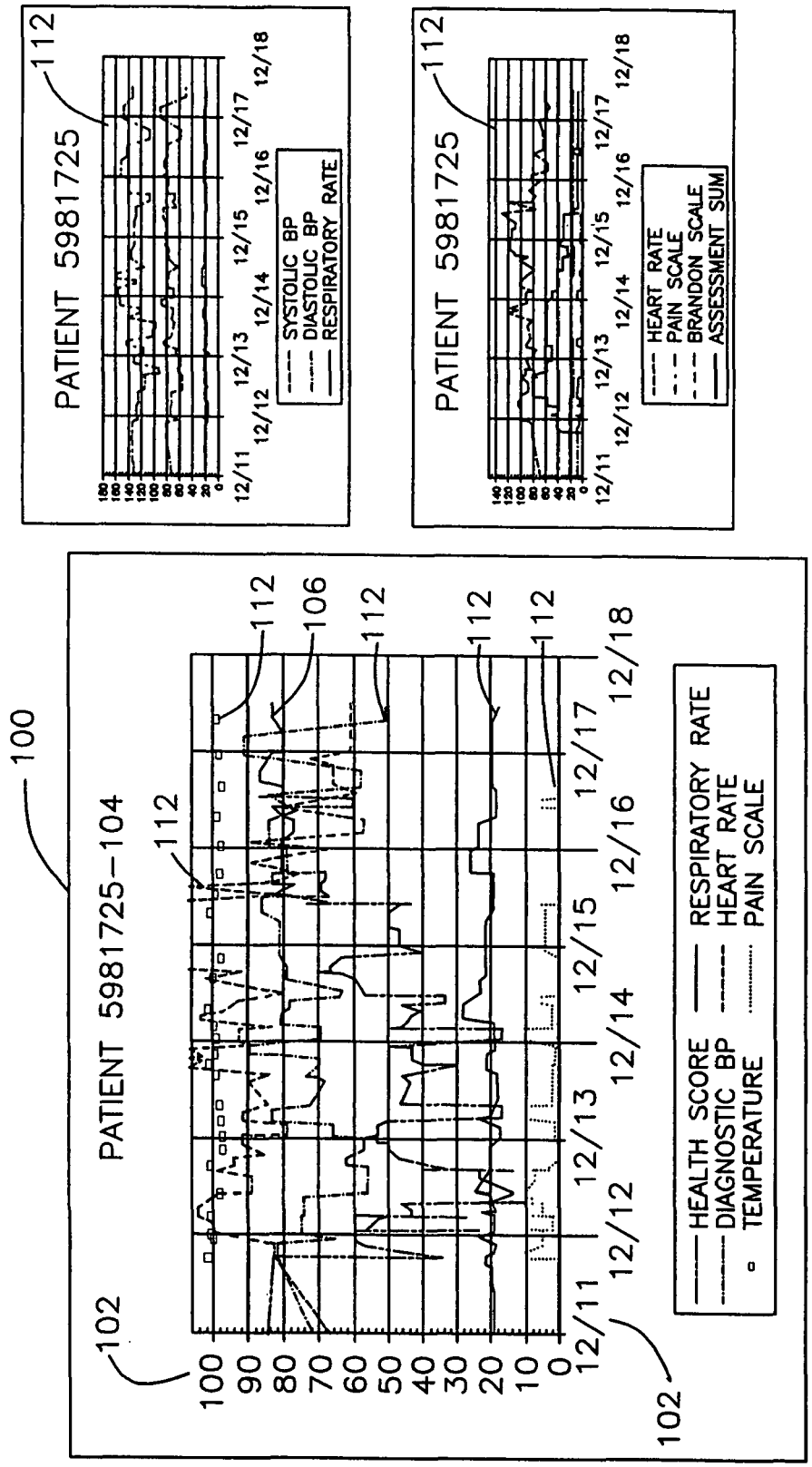
FIG. 7 depicts a sample Health Score chart with principal corresponding measurement curves, in accordance with an illustrative embodiment of the present invention.

Principal corresponding measurement curves 112 may also be generated by comparison module 20 of system 10. The Health Score chart 100 may provide an instant context and patient health trajectory on Health Score plot 106. It is also important for healthcare providers to have access to other direct measurements. FIG. 7 illustrates a typical Health Score chart 100 that includes these direct medical measurements 112. The measurement curves 112 may include but are not limited to: diastolic blood pressure, temperature, respiration rate, pulse, and pain score. This allows healthcare providers to detect other trends that may be affecting the Health Score and, thus, the patient.

In the example in FIG. 7, the patient has a severely reduced Health Score from December 12 through December 15. By looking at the accompanying principal corresponding measurement curves 112, it can be seen that the patient had developed a fever on the 12$^{th}$ and was also dealing with Atrial Fibrillation. By the 16$^{th}$ these conditions had been resolved, with a corresponding sharp increase in Health Score.

Figure 8:
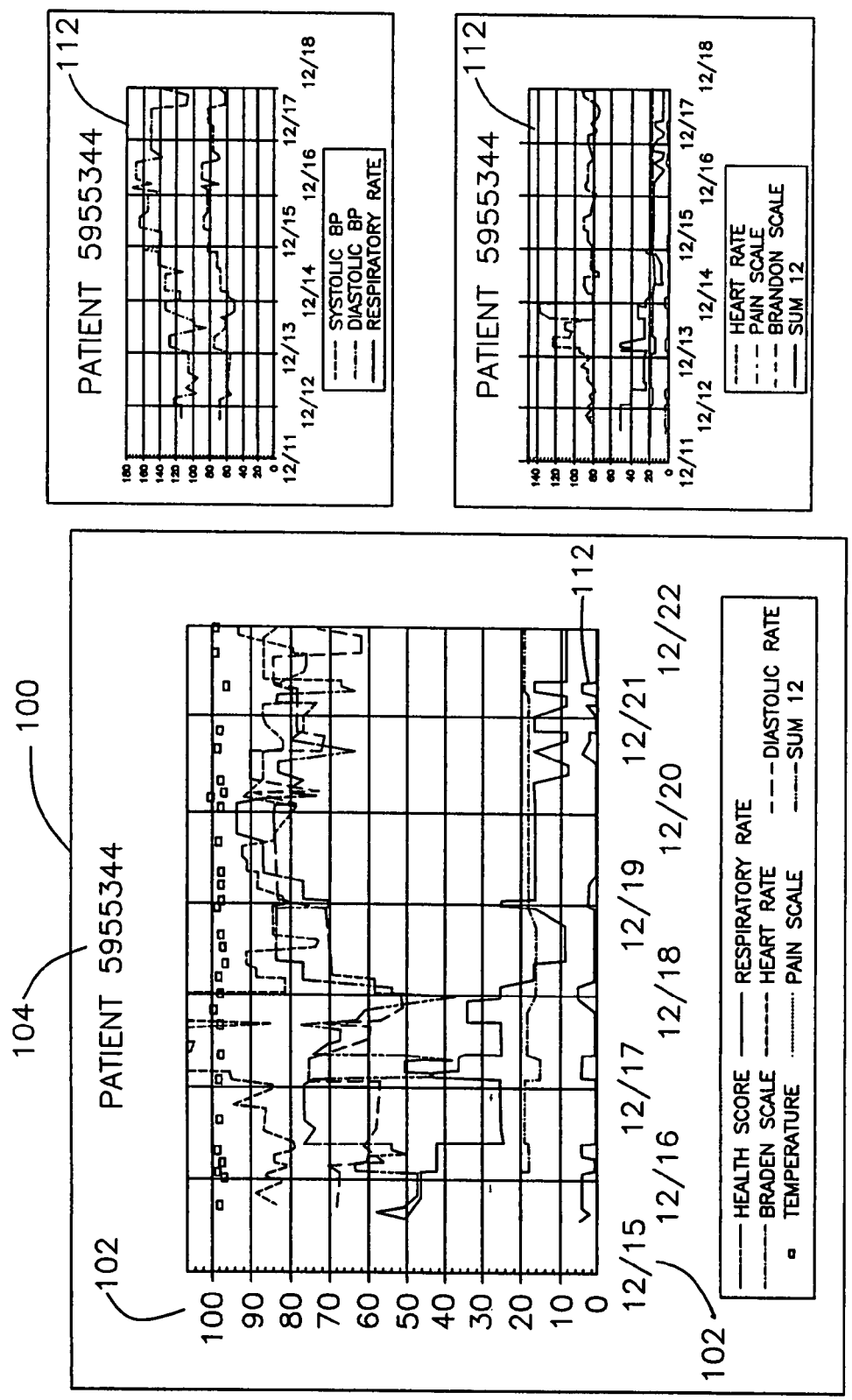
FIG. 8 depicts a sample Health Score chart with principal corresponding measurement curves, in accordance with an illustrative embodiment of the present invention.

FIG. 8 is another example of adding principal corresponding measurement curves 112 to a standard Health Score chart 100. In this example, it can be seen that the Principal Corresponding Measurement curves 112 themselves are important. The line at the bottom of the Health Score chart 100 is "pain scale" which is an evaluation of the patient's pain level. It is scaled between zero and ten. This patient is experiencing significant pain almost exactly every 24 hours. This situation may be the result of a poor pain management strategy; the patient is under-medicated until he experiences a crisis, at which time a large dosage of medication is administered. Evaluation of the chart would prompt modification of this patient's pain medication frequency and dosage.

It is understood that, when using the option of adding direct medical data to the Health Score chart 100, system 10 has the ability to let the healthcare provider select which principal corresponding measurements 112 they would like to see. When the Health Score is improving or is adequate, such features may be toggled off, as they are less important in such instances. They can easily be added to chart 100 if the score on plot 106 again drops, allowing the healthcare provider, optionally, to have additional analysis tools for determining the cause of the drop.

Figure 9:
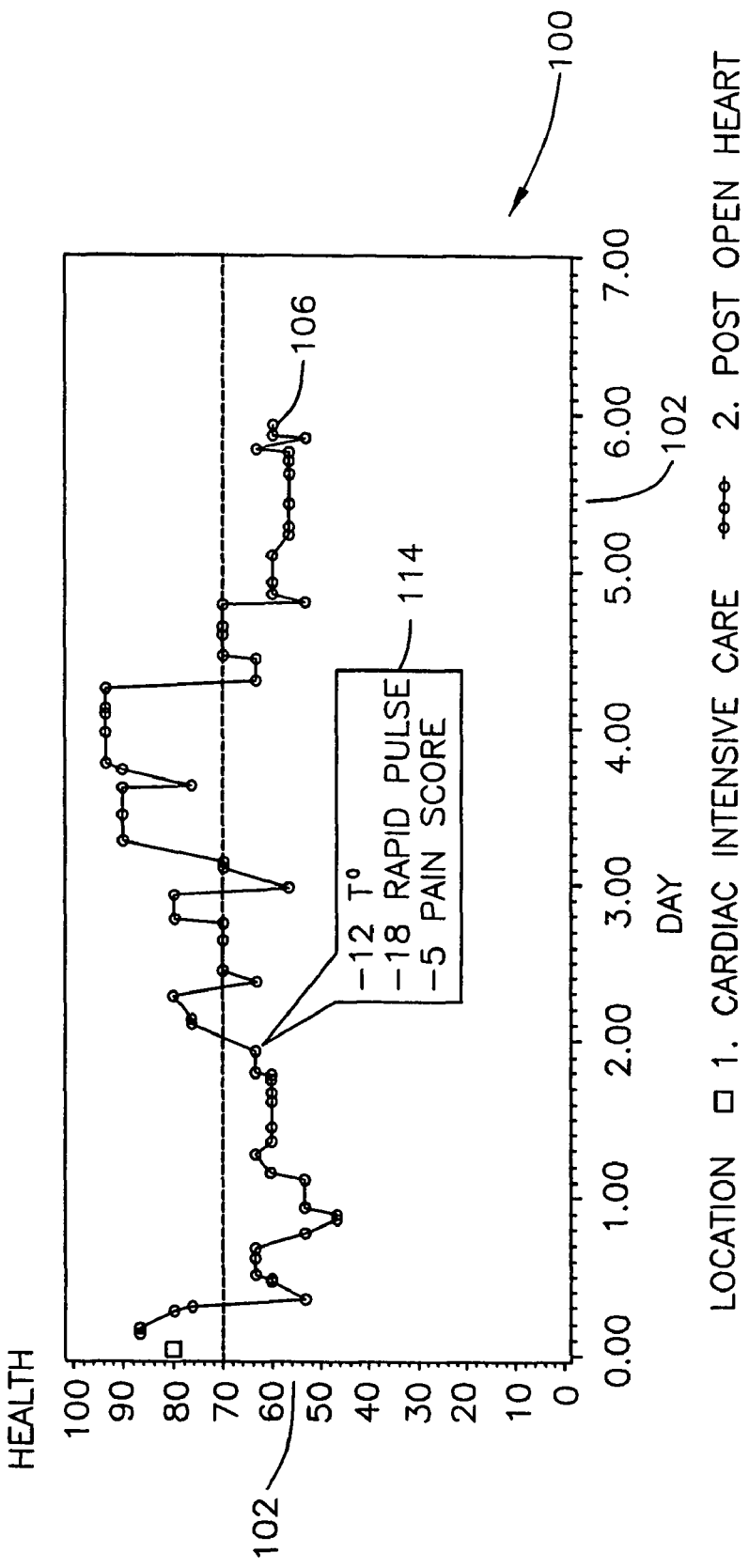
FIG. 9 depicts a sample Health Score chart with a component expansion window, in accordance with an illustrative embodiment of the present invention.

In another embodiment, presentation and/or comparison module 20 may be configured to alter Health Score chart 100, so that when a healthcare provider detects a trend in the Health Score plot 106, they can understand exactly what factors are contributing. To this end, as illustrated in FIG. 9, system 10 may provide for a component expansion window 114, such that if the patient has a Health Score of 65 (for example), the expansion might show that the patient lost 12 points due to elevated temperature (over 101 Fahrenheit), lost 18 points due to rapid pulse (between 100 and 110 beats per minute) and lost 5 points due to a pain score of 5; all out of the perfect Health Score of 100.

Figure 10:
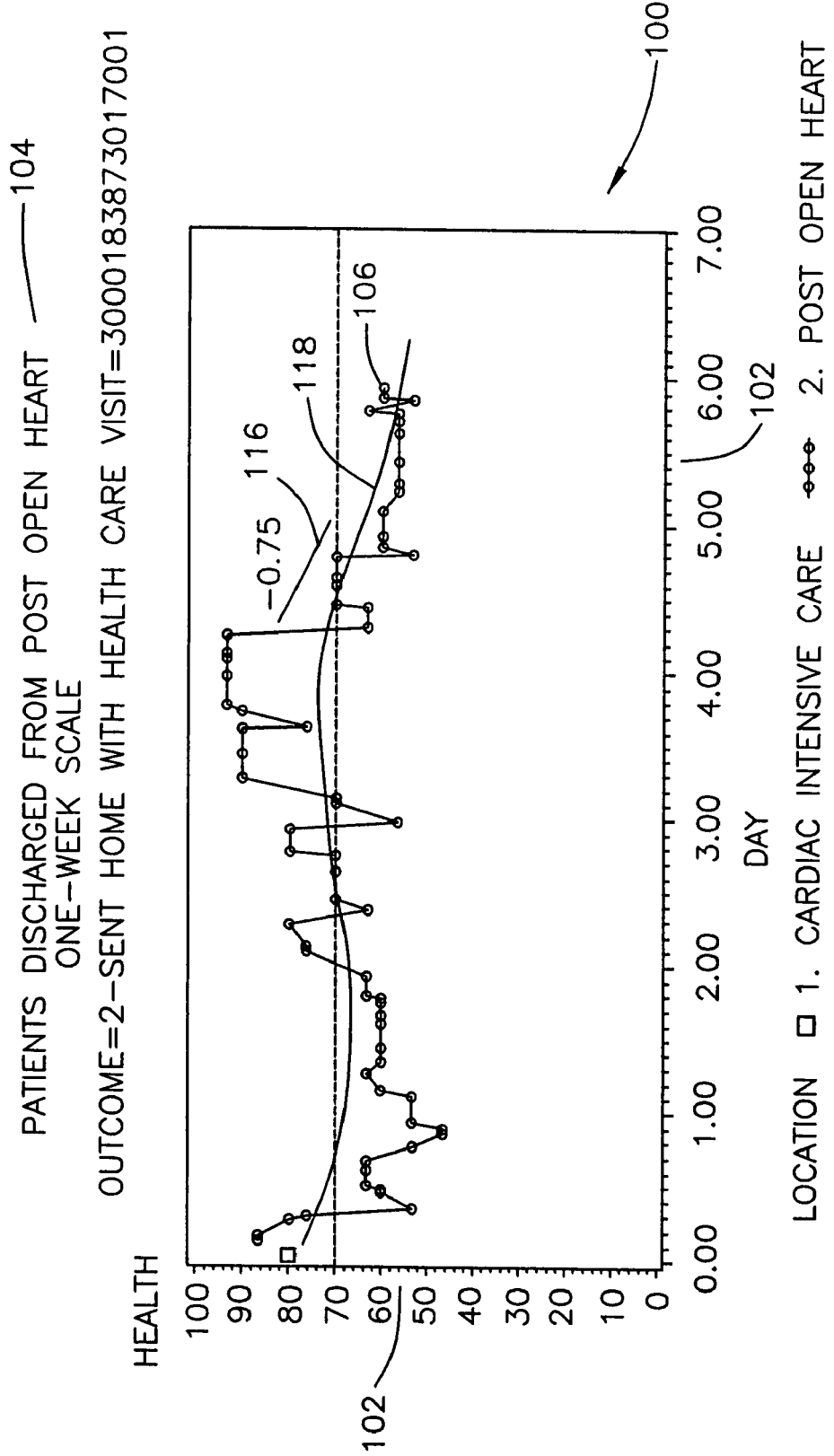
FIG. 10 depicts a sample Health Score chart with slope lines, in accordance with an illustrative embodiment of the present invention.

In another embodiment, presentation and/or comparison module 20 may also alter Health Score chart 100 to obtain certain kinds of slope information. Even though trends are usually easy to spot by eye upon looking at Health Score plot 106, an automatic "simple" slope calculation may also be useful. Mathematically, this is the first derivative of the Health Score as a function of time. Due to the "noisiness" of typical Health Score plots 106, some averaging methods may be employed as well. If the slope is positive, the patient is probably getting better; if it is approximately zero, then the patient is staying the same; and if it is negative, then the patient is probably getting worse. Slope lines 116 may be added to the Health Score plot 106, as shown in FIG. 10. Such slope information may help identify trends in Health Score plot 106, particularly, when plot 106 is "noisy" due to large variations between each Health Score measurement. Although normally "staying the same" would not be considered a negative, in the situation where the patient is expected to be recuperating, "staying the same" may be quite worrisome. In the present example, although the most recent Health Scores on plot 106 are constant at about a level of 70, the slope line 116 shows a negative slope, taking into account prior points, including a time early on day 4 when the score was closer to 90.

Presentation and/or comparison module 20 of system 10 may also compute "rate of change" of the simple slope. For instance, although the patient is still getting better, the rate of improvement may be decreasing. This slow-down in recovery could be evidence of a problem just beginning to develop. Mathematically, this curvature information is the second derivative of Health Score as a function of time. Similar to the slope data 116, due to the "noisiness" of the curves, averaging is included in the computation. It is understood that attending physicians can adjust the slope calculation to include more or less reference Health Scores from plot 100 depending on the time span over which the physician intends to analyze.

The Health Score may be calculated continuously for a patient's entire hospital stay and/or recovery period and any or all of that information may be displayed on the screen. In some embodiments, the graph may display the patient's Health Score during his/her entire hospital stay, thereby enabling the healthcare provider to look at one screen and be able to understand the patient's health history, as opposed to having to flip through hundreds of pages of a patient's medical history. In some embodiments, the time span over which the Health Score is plotted may be a patient's entire hospital stay, the patient's stay in a certain ward, such as the ICU or ER, the past few days of the patient's stay, a number of hours (such as 3, 5, 10, 12, 13 or more hours), days, weeks or months, or any length of time as not all embodiments are intended to be limited in this respect. In some embodiments, the chart may contain compressed or selective data from a period of time and full data from a different period of time. For example, if a patient has been in a hospital for a month, the most recent three days may be depicted by hourly Health Scores, while the rest of the month, prior to those three days, may be depicted by a daily summary point on the chart.

When the raw data is noisy, a "running average" or other "smoothing" of the Health Score can be displayed on Health Score charts. The smoothed Health Score curve 118, shown in FIG. 10, could incorporate both the $1^{st}$ derivative (slope) and/or the $2^{nd}$ derivative (curvature) by color-coding or by thickness of the displayed line. For example, if the patient was getting worse (negative slope), the line might be colored red. If the patient is getting worse at an accelerating rate, or is getting better at a lessening rate, then the line could be bolded for emphasis.

Figure 11:
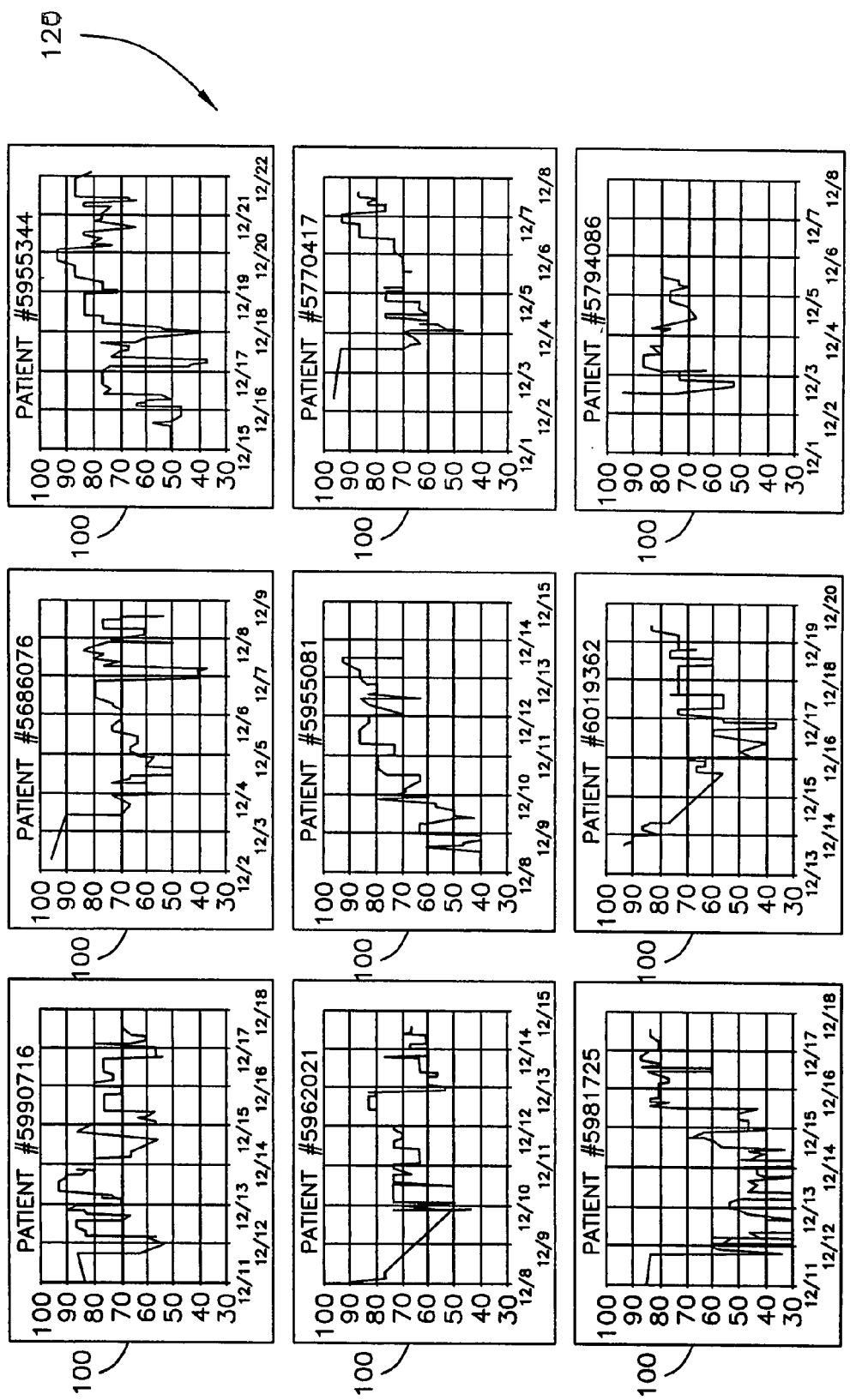
FIG. 11 depicts a panel of Health Score charts, in accordance with an illustrative embodiment of the present invention.

Presentation and/or comparison module 20 may further display a panel of Health Score charts 120, as shown in FIG. 11. Typically, a nurse or a doctor or a unit supervisor wants to see, on a single page, the graphs for all the patients in their care. Therefore, system 10 may provide for the creation of a patient panel 120, displaying a series of Health Score charts 100. Patient IDs can be included in the label data 104 to identify each chart 100 on panel 120. This is especially useful because an attending physician may wish to appoint more of his time to patients with falling Health Scores (rather than rising ones), given that those patients with falling scores will likely require more attention and given that the physician's time is usually very limited.

It is understood that such modifications to patient Health Score charts 100 are intended only as example modification and are in no way intended to limit the scope of the present invention. Any similar invention that utilizes modified Health Score charts 100 is also within the contemplation of the present invention.

In one embodiment, fifty potential variables may be used from data readily available in the patient's records. For some or all potential variables, excess risk as a function of the variable may be computed, as measured by one-year mortality. The computed excess risk may be the additional mortality risk above the risk for the variable's minimum mortality. In order to provide the Health Score with continuous input functions of each of these variables, the plots of 1-year mortality may be compared with each variable to higher order polynomials. With all variables on a common risk scale, the relative importance of variables may be determined by using stepwise logistic regression. Two variable sets (with a total of twenty-six variables) may be built, one which incorporates data inputted approximately every 4-6 hours (vital sign and nursing assessments) and the other including data from blood chemistry panels and blood analysis.

Each set of variables may be used to construct a model scaled from zero to 100, so that the best health would be represented by a value of 100 and the worst health be represented by a value of zero. The Health Score may consist of a linear combination of these two models weighted by two factors: a scaling factor, to bring the absolute values of the two models into alignment, and a time-dependent factor, used to determine the proportion of the more slowly refreshed chemistry panel model, whose contribution decays to zero over 48 hours as the data ages.

The Health Score may use 26 variables, for example, vital signs, including temperature, systolic blood pressure, diastolic blood pressure, heart rate, blood oxygen saturation and respiratory rate; nursing assessments, including cardiac, food/nutrition, gastrointestinal, genitourinary, musculoskeletal, neurological, peripheral vascular, psycho-social, respiratory, skin/tissue and safety/fall risk standards; scores, including Braden Scale Heart patterns; blood chemistry, including blood urea nitrogen, creatinine, chloride, sodium and potassium; and blood analysis, including hemoglobin and white blood cell count.

In one embodiment of the present invention, as illustrated in FIG. 1, alert module 22 may send an alert to an attending physician or supervising nurse that a Health Score of a particular patient has fallen below a pre-determined threshold at step 220. For example, if an attending physician sets a threshold of 70, then patients falling below such a level may cause alert module 22 to send an alert message to system terminal 10B at nursing station 32. Although the physician may wish to see Health Score charts 100, regardless of the alerts, alert module 22 may act as a reserve precaution warning of the general failing health conditions of a patient who may be approaching a crisis situation. It is understood that the alert may actually be set to an upper threshold as well. Keeping physicians aware of improving health conditions of certain patients may be useful in making discharge decisions or in adjusting medication. Alerts may also be triggered by a fall of so many points in Health Score or by a slope that is of a sufficient negative magnitude.

As such, the above-described system 10 and accompanying generated Health Score charts 100 may provide a convenient means for monitoring patient health status, particularly in hospital post-operational situations. It may allow doctors to get a feel for the overall health of the patient and to detect trends in the patient's health. Such information is particularly useful in preventing crisis situations from arising in patients, where the worsening condition (of a patient of adequate, yet deteriorating health) is overlooked until it is too late. The creation of the Health Score chart 100, by the present invention, may help in alerting attending physicians, nurses, or "rapid response teams" to deteriorating conditions, even when a spot check of the patient's health would seem to show the patient to be in an adequate state of health.

In addition to the uses outlined above, the Health Score can be used for statistical analysis. For example, the Health Score and the Health Score charts 100 can be used in retrospective research. Many studies of drugs and procedures are published monthly. These studies would benefit from the inclusion of a readily computable Health Score.

For example, a procedure is often evaluated in terms of mortality rate, length of hospital stay, or number of re-admissions to the hospital. These measures are all significant, but at the same time are all rather crude measures. For example, if "Procedure A" has a mortality rate of 0.5% and "Procedure B" has a mortality rate of 0.7%, it may be very difficult to judge one the superior of the other, using only these mortality statistics. However, if patients discharged after Procedure A have an average Health Score of 80, and those discharged after Procedure B have an average Health Score of 60, there may be a real and meaningful difference between the two procedures in terms of overall efficacy in treating the patient. Thus, system 10 may provide a more sensitive measurement of health than any other available measure, since it is not based solely on major "outcomes" (like discharge or death), but rather on a more subtle combination of overall health factors. A medical study using the Health Score, which this invention makes readily available for every patient, may find earlier and easier and more meaningful "statistical significance" than a similar study that needed to wait for eventual mortality outcomes.

Figure 12:
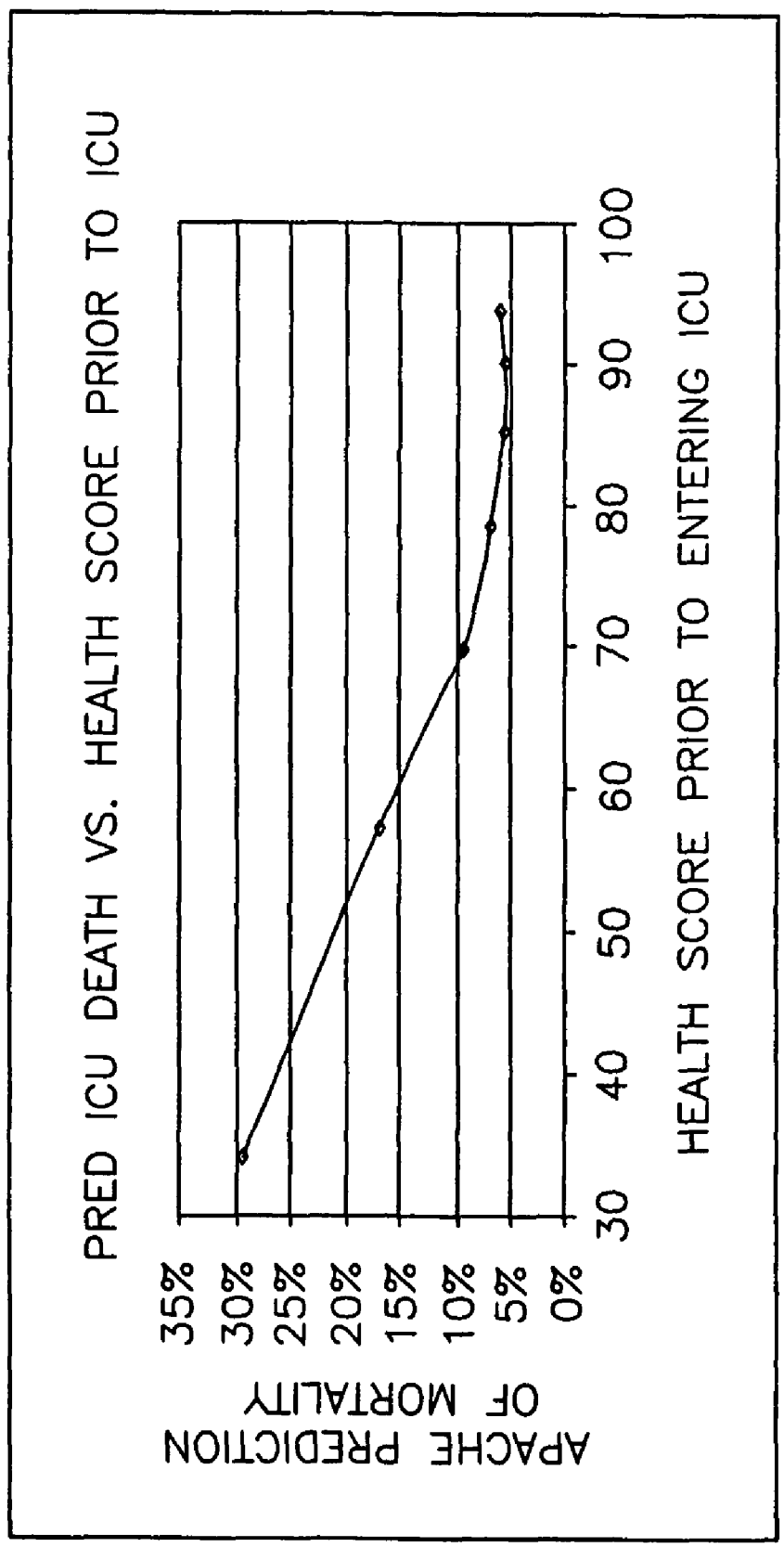
FIG. 12 depicts a chart showing a correlation between patient Health Scores and rate of predicted expiration, in accordance with an illustrative embodiment of the present invention.

An additional feature of Health Scores generated by system 10 is that the Health Score can be used as a predictor to assist in determining which patients require the most care. Although individual symptoms and raw medical data may be varied, the amalgamated Health Score, as shown on Health Score charts 100, tends to be an accurate predictor of patient outcome. For instance, using Health Score data generated postfacto, FIG. 12 shows actual graphic correlation between Health Scores from system 10 (computed at transfer to the ICU from a regular ward of the hospital) versus the rate of predicted expiration after an ICU stay. The chart shows a precipitous decline in survival rates when the patient has, incoming to the ICU, an overall Health Score below 65. In such instances, ICU units admitting patients with Health Scores below 65 may choose to divert additional resources to these patients, in order to reduce morbidity and mortality rates. The Health Score is a sensitive new tool for the ICU use. In this example, patient "A" with a Health Score of 65, versus patient "B" with a Health Score of 75, might not exhibit obviously different symptoms, and thus the patients might be treated similarly if the Health Score were not available. But when the doctors know that there is a statistically significant decline in survival rate when the Health Score is 65, patient "A" may get the additional care that would save his life.

Furthermore, incoming Health Scores can be used as an indicator of survival rates before undergoing certain procedure. Not all patients are equal when entering the hospital for a procedure. In some cases, a decision "not to operate" may be made if the risks of complication are too great. An admission-timed Health Score from system 10 may also provide statistical information for post-operative survival rates, which could greatly influence a hospital's decision to recommend the use of surgery, versus alternative treatments.

In some embodiments, the system may allow physicians and nurses and clinical researchers to provide more effective health care for each patient, especially those spending several days in a hospital. In some embodiments, hospitals may avoid errors and reduce crisis management by using the system's ability to detect trends in a patient's health before the patient reaches a crisis point. Recognizing a serious decline soon enough to administer proper treatment may be a life-saving benefit. In some embodiments, the system may give physicians and nurses a way in which to get the "big picture" of a patient's condition and absorb in a glance perhaps 100 pages of a patient's medical records. This deeper understanding, along with this new capability to detect health trends, both short-term (over the space of hours), and long-term (over the space of days), may be important in delivery of effective medical care. In some embodiments, an entirely new field of scientific study may be enabled, where medical and surgical treatments can be evaluated by the new measurements provided by some of the systems disclosed herein In some embodiments, a new measurement of health is generated, herein termed the patient "Health Score" which may be continually plotted and displayed to show a patient's medical progress during his/her hospital stay. Some embodiments of the present invention may prove to be a vital aid for improving the quality and continuity of medical care.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

Example #1

Figure 13:
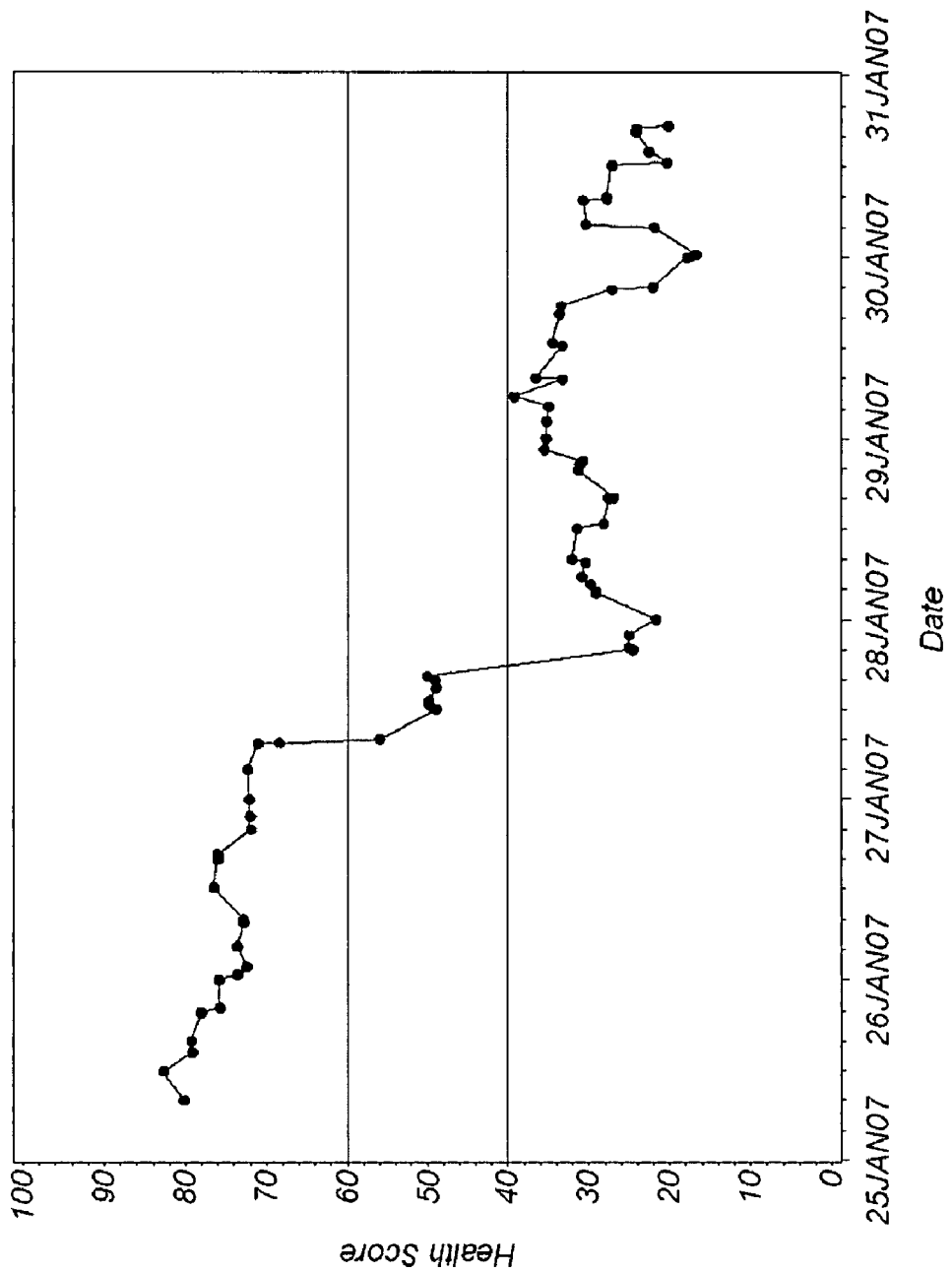
FIG. 13 depicts a chart showing a patient's Health Score, in accordance with the illustrative embodiment of Example #1.

As depicted in the embodiment shown in FIG. 13, a patient was admitted with complaints related to a foot problem. The patient's history included chronic alcoholism. For two days the patient was stable at a Health Score of about 70. The following day the patient's Health Score dropped from 70 to 50, remained at that level for 5 hours, then the Health Score dropped from 50 to 20, a total of a 50 point drop over a total of 12 hours. During this time the doctors' and nurses' notes reflect no clear indication that the patient had moved from a stable situation to one in which the patient was at risk of dying. The patient remained at a low Health Score for 3 days at which point the patient died. One of the physicians involved indicated that if he/she had understood that there had been a significant change in the patient's status, the physician would have reevaluated the treatment, altered it and possibly prevented the patient's death.

Example #2

Figure 14:
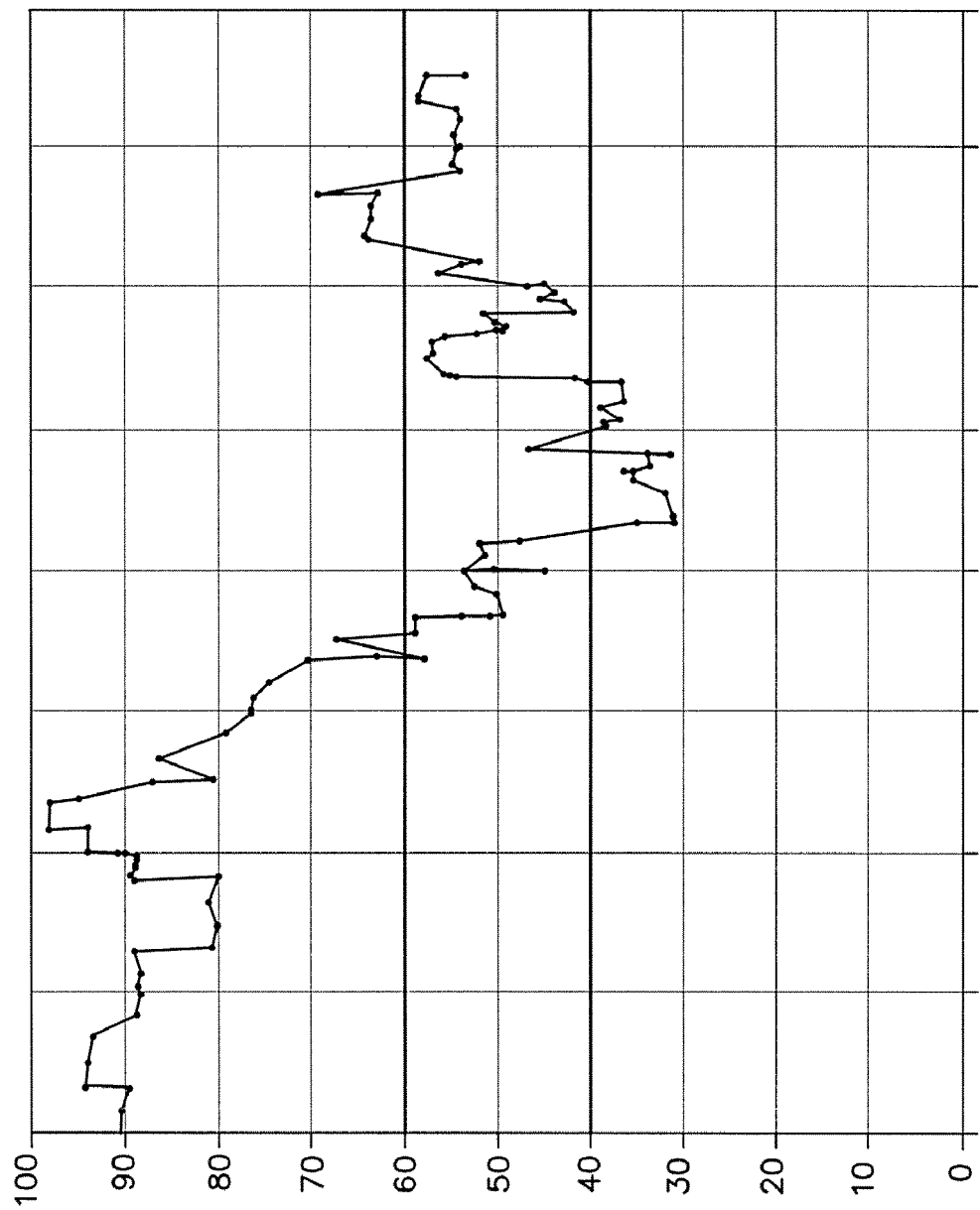
FIG. 14 depicts a chart showing a patient's Health Score, in accordance with the illustrative embodiment of Example #2.

As depicted in the embodiment shown in FIG. 14, a patient entered the hospital with a complaint of jaundice. At the end of day 2 laparoscopic surgery was performed to remove gallstones. For the next three days the patient's Health Score declined from almost 100, which would have been normal following corrective surgery, to 30, indicating significant risk of death. The patient received several transfusions due to a report of anemia. It was only at day 4 that it was realized that a complication had occurred. At day 5 exploratory surgery was performed which found and corrected a source internal bleeding. Following this, the patient recovered to a Health Score of 60. FIG. 14 does not cover the period until discharge If the Health Score chart had been available, the complication would have been detected at the end of day 3 when the Health Score was still above 60, instead of at days 4 and 5 when the Health Score had dropped to 30. Earlier detection would have not only reduced the patient's risk of death, but it would have shortened the patient's length of stay in the hospital and significantly lessened the patient's suffering.

What is claimed is:

1. A method for generating an indicator of a patient's health comprising:
continually receiving, on a computer, disparate medical data relating to a patient at a plurality of time points over a period of time, the data including subjective data determined by a nurse after performing a musculoskeletal nursing assessment including a subjective evaluation by the nurse of the patient's ability to move all extremities independently;
transforming, on the computer, for each of the plurality of time points, the disparate medical data into number values so that the disparate medical data can be combined;
combining, on the computer, for each of the plurality of time points, the number values to generate a single output value that represents the health of the patient at each of the plurality of time points; and
continually plotting and displaying, on the computer, a graph of each of the single output values for each of the plurality of time points, wherein the graph shows the patient's health trajectory over the period of time.

2. The method of claim 1 wherein the musculoskeletal nursing assessment includes a subjective evaluation by a nurse after assessing the patient's ability to perform functional activities as observed or stated.

3. The method of claim 1 wherein the disparate medical data includes objective data selected from the group consisting of diastolic blood pressure, temperature, respiration, systolic blood pressure, and heart rate.

4. The method of claim 1 wherein at least one of the time points represents a period of time after the patient has undergone a surgical procedure.

5. The method of claim 1 wherein the graphical display of the patient's health trajectory is viewed by a remote health service provider located remotely from the patient.

6. The method of claim 1 further comprising repeating all of the steps for many patients, and presenting a single image showing such graphs, color-coded by the single output value, allowing a nurse or doctor to view and evaluate many patients simultaneously.

7. The method of claim 1 wherein a reference line stored on the computer is added to the graph, the reference line representing an average health trajectory for patients who have had a same procedure or who are being treated for a same disease, so that the patient's progress can be compared to average progress.

8. A method for generating an indicator of a patient's health comprising:
   continually receiving, on a computer, disparate medical data relating to a patient at a plurality of time points over a period of time, the data including subjective data determined by a nurse after performing a gastrointestinal nursing assessment including a subjective evaluation by the nurse of the patient's bowel sounds;
   transforming, on the computer, for each of the plurality of time points, the disparate medical data into number values so that the disparate medical data can be combined;
   combining, on the computer, for each of the plurality of time points, the number values to generate a single output value that represents the health of the patient at each of the plurality of time points; and
   continually plotting and displaying, on the computer, a graph of each of the single output values for each of the plurality of time points, wherein the graph shows the patient's health trajectory over the period of time.

9. The method of claim 8 wherein the gastrointestinal nursing assessment includes a subjective evaluation by a nurse after assessing a factor selected from the group consisting of feel and appearance of the patient's abdomen, presence of nausea in the patient, presence of vomiting in the patient, the patient's continence and the patient's bowel patterns.

10. The method of claim 8 wherein the disparate medical data includes objective data selected from the group consisting of diastolic blood pressure, temperature, respiration, systolic blood pressure, and heart rate.

11. The method of claim 8 wherein at least one of the plurality of time points represents a period of time after the patient has undergone a surgical procedure.

12. The method of claim 8 wherein the graphical display of the patient's health trajectory is viewed by a remote health service provider located remotely from the patient.

13. The method of claim 8 further comprising repeating all of the steps for many patients, and presenting a single image showing such graphs, color-coded by the single output value, allowing a nurse or doctor to view and evaluate many patients simultaneously.

14. The method of claim 8 wherein a reference line stored on the computer is added to the graph, the reference line representing an average health trajectory for patients who have had a same procedure or who are being treated for a same disease, so that the patient's progress can be compared to average progress.

15. A method for generating an indicator of a patient's health comprising:
   continually receiving, on a computer, disparate medical data relating to a patient at a plurality of time points over a period of time, the data including subjective data determined by a nurse after performing a nursing assessment including a subjective evaluation by the nurse using a Braden Scale;
   transforming, on the computer, for each of the plurality of time points, the disparate medical data into number values so that the disparate medical data can be combined;
   combining, on the computer, for each of the plurality of time points, the number values to generate a single output value that represents the health of the patient at each of the plurality of time points; and
   continually plotting and displaying, on the computer, a graph of each of the single output values for each of the plurality of time points, wherein the graph shows the patient's health trajectory over the period of time.

16. The method of claim 15 wherein the disparate medical data includes objective data selected from the group consisting of diastolic blood pressure, temperature, respiration, systolic blood pressure, and heart rate.

17. The method of claim 15 wherein at least one of the plurality of time points represents a period of time after the patient has undergone a surgical procedure.

18. The method of claim 15 wherein the graphical display of the patient's health trajectory is viewed by a remote health service provider located remotely from the patient.

19. The method of claim 15 further comprising repeating all of the steps for many patients, and presenting a single image showing such graphs, color-coded by the single output value, allowing a nurse or doctor to view and evaluate many patients simultaneously.

20. The method of claim 15 wherein a reference line stored on the computer is added to the graph, the reference line representing an average health trajectory for patients who have had a same procedure or who are being treated for a same disease, so that the patient's progress can be compared to average progress.

* * * * *